United States Patent [19]
Levine et al.

[11] Patent Number: 5,417,714
[45] Date of Patent: May 23, 1995

[54] DDI PACING WITH PVC-PROTECTED HYSTERESIS AND AUTOMATIC AV INTERVAL ADJUSTMENT

[75] Inventors: Paul A. Levine, Santa Clarita, Calif.; Malcolm Clarke, Stoke-On-Trent, England; John W. Poore, South Pasadena; Jason A. Sholder, Beverly Hills, both of Calif.

[73] Assignee: Pacesetter, Inc., Sylmar, Calif.

[21] Appl. No.: 60,765

[22] Filed: May 11, 1993

Related U.S. Application Data

[63] Continuation-in-part of Ser. No. 846,308, Mar. 5, 1992, Pat. No. 5,237,992.

[51] Int. Cl.⁶ .............................................. A61N 1/36
[52] U.S. Cl. .................................................... 607/9
[58] Field of Search ........................... 607/9, 15, 18, 25

[56] References Cited

U.S. PATENT DOCUMENTS

| | | | |
|---|---|---|---|
| 4,363,325 | 12/1982 | Roline et al. | 128/419 |
| 4,561,442 | 12/1985 | Vollmann et al. | 128/419 |
| 4,562,841 | 1/1986 | Brockway et al. | 128/419 |
| 4,590,944 | 5/1986 | Mann et al. | 128/419 |
| 4,712,555 | 12/1987 | Thornander et al. | 128/419 |
| 4,726,380 | 2/1988 | Vollmann et al. | 128/419 |
| 4,788,980 | 12/1988 | Mann et al. | 128/419 |
| 4,920,965 | 5/1990 | Funke et al. | 128/419 |
| 4,940,052 | 7/1990 | Mann et al. | 128/419 |
| 4,944,298 | 7/1990 | Sholder | 128/419 |
| 4,967,746 | 11/1990 | Vandegriff | 607/9 |
| 5,103,820 | 4/1992 | Markowitz | 607/9 |
| 5,237,992 | 8/1993 | Poore | 607/25 |

FOREIGN PATENT DOCUMENTS 0318304  5/1989  European Pat. Off. ........... 607/9

*Primary Examiner*—William E. Kamm
*Assistant Examiner*—Marianne Parker
*Attorney, Agent, or Firm*—Malcolm J. Romano; Harold C. Schloss; Samuel M. Katz

[57] ABSTRACT

A dual-chamber pacemaker provides DDI pacing with PVC-protected hysteresis and automatic AV interval adjustment. An extended hysteresis atrial escape interval ($AEI_H$) is invoked in response to the occurrence of either an atrial paced event followed by a sensed R-wave (an AR event), or an atrial sensed event followed by a sensed R-wave (a PR event). The occurrence of a premature ventricular contraction (PVC) thus does not trigger $AEI_H$. In one embodiment, $AEI_H$ is not invoked unless the sensed AR or PR interval exceeds a prescribed reference interval. In a further embodiment, the AV interval (AVI) associated with the DDI operation is automatically shortened following an atrial stimulation pulse (A-pulse) delivered upon the timing-out of the $AEI_H$. The shortened AVI is maintained for a programmed number of cycles of DDI operation, after which a lengthened AVI is reestablished for one cycle. If AV pacing follows after using the lengthened AVI, then the shortened AVI is reinstated for a second number of programmed cycles of DDI operation. If AR pacing follows after using the lengthened AVI, signifying intact AV nodal conduction, then the AVI is lengthened to the programmed AVI over a prescribed number of cycles.

24 Claims, 5 Drawing Sheets

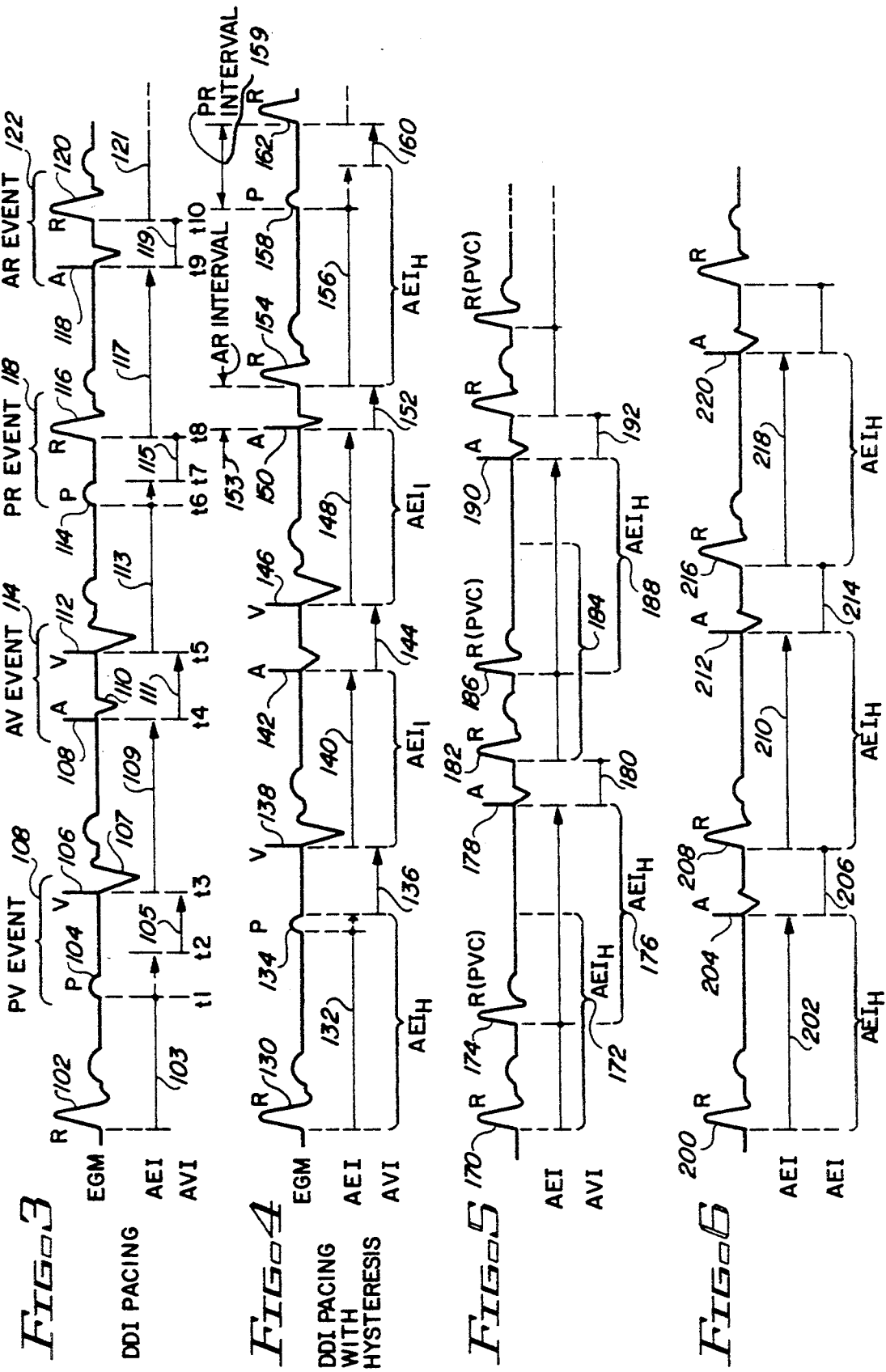

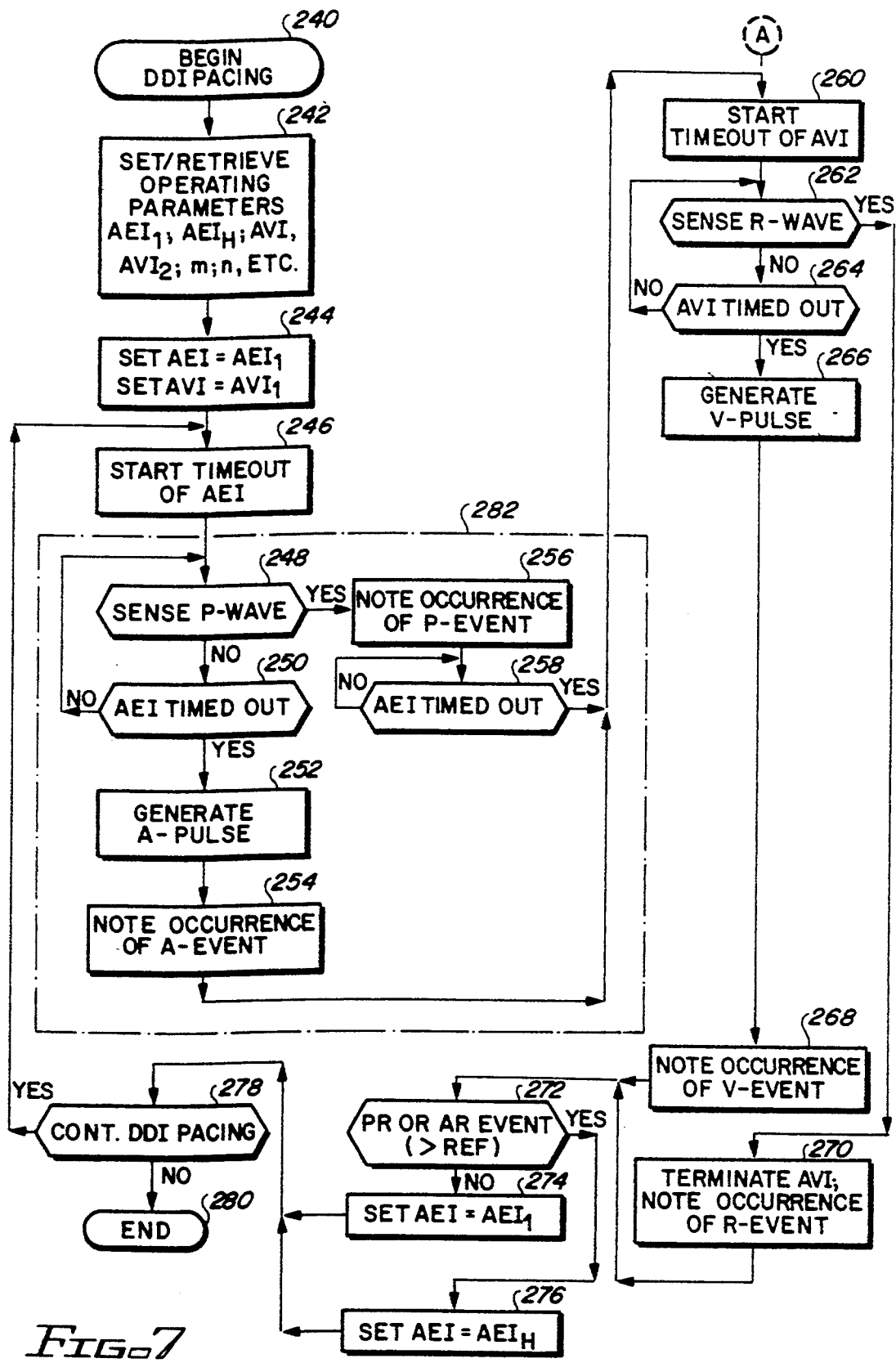

DDI PACING WITH PVC-PROTECTED HYSTERESIS AND AUTOMATIC AV INTERVAL ADJUSTMENT

CROSS-REFERENCE TO RELATED APPLICATIONS

The present application is a continuation-in-part of application Ser. No. 07/846,308, filed Mar. 5, 1992, now U.S. Pat. No. 5,237,992.

BACKGROUND OF THE INVENTION

Field of the Invention

The present invention relates to implantable medical devices and methods, and more particularly, to an implantable dual-chamber pacemaker configured to provide PVC-protected hysteresis and automatic AV interval adjustment in the DDI pacing mode.

The basic function of the heart is to pump blood (circulate) throughout the body delivering oxygen and nutrients to the various tissues while removing waste products and carbon dioxide. The heart is divided into four chambers comprised of two atria and two ventricles. The atria are the collecting chambers holding the blood which returns to the heart until the ventricles are ready to receive this blood. The ventricles are the primary pumping chambers. The pumping function of the heart is achieved by a coordinated contraction of the muscular walls of the atria and the ventricles.

The heart is commonly thought of as having two sides, the right side and the left side. Blood returning to the heart from the body (legs, arms, head, abdomen) returns to the right atrium. From there, it goes to the right ventricle from which it is pumped to the lungs. In the lungs, the carbon dioxide collected from the body is exchanged for oxygen.

The oxygenated blood then travels to the left atrium from which is enters the left ventricle. The left ventricle is the major pumping chamber circulating the blood to the remainder of the body.

The atria are more than simple collecting chambers. The atria contain the heart's own (natural, native or intrinsic) pacemaker that controls the rate at which the heart beats or contracts. In addition, the atrial contraction helps to fill the ventricle, further contributing to optimal filling and thus maximizing the amount of blood which the heart is able to pump with each contraction. Hence, atrial contraction is followed after a short period of time (normally 120 to 200 ms) by ventricular contraction.

The period of cardiac contraction during which the heart actively ejects the blood into the arterial blood vessels is called systole. The period of cardiac relaxation during which the chambers are being filled with blood is called diastole. Atrial and ventricular systole are sequenced allowing the atrial contraction to help optimally fill the ventricle. This is termed AV synchrony.

A cardiac cycle comprises one sequence of systole and diastole. It can be detected by the physician by counting the patient's pulse rate. It is also reflected by the cardiac rhythm as recorded by an electrocardiogram. The electrocardiogram (ECG) records the electrical activity of the heart as seen on the surface of the body. The electrical activity refers to the cardiac depolarization in either the atrium and/or ventricle. On the ECG, the atrial depolarization is represented by the P-wave while the ventricular depolarization is represented by the QRS complex, sometimes abbreviated as an "R-wave". The electrical depolarization triggers or initiated the active muscular contraction. Once the cardiac cells are depolarized, they must repolarize in order for the next depolarization and contraction to occur. Ventricular repolarization is represented by the T-wave. Atrial repolarization is rarely seen on an ECG as it occurs at virtually the same time as the R-wave and is hidden by this large electrical signal.

A normal heart rate varies between 60 to 100 beats per minute (bpm) with an average of 72 bpm resulting in approximately 100,000 heart beats per day. The heart beat normally increases during period of stress (physical or emotional) and slows during periods of rest (sleep).

The amount of blood that the heart pumps in one minute is called the cardiac output. It is calculated by the amount of blood ejected with each heart beat (stroke volume) multiplied by the number of heart beats in a minute. If the heart rate is too slow to meet the physiologic requirements of the body, the cardiac output will not be sufficient to meet the metabolic demands of the body. One of two major symptoms may result. If the heart effectively stops with no heart beat, there will be no blood flow and if this is sustained for a critical period of time (10 to 30 seconds), the individual will faint. If there is a heart beat but it is too slow, the patient will be tired and weak (termed low cardiac output).

Too slow a heart beat is termed a bradycardia. Any heart rate below a rate of 60 bpm is considered a bradycardia. However, a bradycardia only needs to be treated if it is causing the individual to .have symptoms. If it is a persistent abnormality and is causing symptoms, implantation of a permanent cardiac pacemaker is often prescribed.

A pacemaker may also be referred to as a pacing system. The pacing system is comprised of two major components. One component is the pulse generator which includes the electronic circuitry and the power cell or battery. The other is the lead or leads which connect the pacemaker to the heart.

Pacemakers are described as either single chamber or dual chamber systems. A single chamber system stimulates and senses the same chamber of the heart (atria or ventricle). A dual chamber system stimulates and/or senses in both chambers of the heart (atria and ventricle).

The pacemaker delivers an electrical stimulus to the heart to cause the heart to contract when the patient's own intrinsic rhythm fails. In this way, the pacemaker can help to stabilize the electrical rhythm of the heart.

The basic function of a pacemaker can be generically described by a five letter code. The first three letters refer specifically to electrical stimulation for the treatment of bradycardias. The fifth position refers to electrical stimulation therapy for the primary treatment of fast heart rhythms or tachyarrhythmias or tachycardias. The fourth position reflects the degree of programmability and rate modulation.

The first position of the code identifies the chamber to which the electrical stimulus is delivered. If the device is not capable of bradycardia support pacing, a "O" would occupy this first position. If the unit paces in the ventricle, this is identified by a "V" while an "A" indicates that it can deliver the stimulus to the atrium. If stimuli can be delivered to either the atrium or ventricle, the letter "D" is used to reflect dual chamber stimulation.

The second position of the code identifies the chamber or chambers in which sensing occurs. Sensing is the ability of the pacemaker to recognize the intrinsic electrical activity of the heart. The letters used in this position are identical to those used in the first position.

The third position identifies the way the pacemaker responds to a sensed signal. An "I" means that the pacemaker will be inhibited. That is, when the pacemaker senses or sees an intrinsic electrical signal, it inhibits its own output pulse and resets one or more internal timers within the pacemaker's circuitry. The other basic response is represented by a "T" which means triggered. The triggered mode of response indicates that when the pacemaker senses an intrinsic electrical signal, it not only resets various internal timers within the pacemaker, it also initiates or releases a stimulus in response to that sensed event. An output pulse is said to be triggered. "D" in this position refers to both modes of sensing response. Most commonly, a sensed signal arising from the atrium and sensed on the atrial channel of a dual chamber pacemaker will inhibit the atrial output but trigger a ventricular output after a brief delay (the AV interval). If a native ventricular depolarization does not occur before the AV delay timer completes, a ventricular stimulus will be released at the end of this AV delay. If a native ventricular signal is sensed within the AV interval, the ventricular output will be inhibited and other timers will be reset. If a native ventricular signal is sensed before the atrial stimulus is released, both the atrial and ventricular output pulses will be inhibited and the various timers will be reset.

The fourth position is unique. It reflects the degree of programmability and rate modulation. It also reflects a hierarchy of capabilities. An "O" in the fourth position indicates that the pacemaker cannot be noninvasively adjusted or programmed. Programming is the ability to adjust or change the parameters of the pacemaker from outside the body without requiring a repeat operation. It is usually accomplished by a series of critically timed magnetic or radio frequency (rf) pulses controlled by a special device termed a programmer. The letter "p" in the fourth position refers to simple programmability, namely only one or two parameters can be programmed. The letter "M" in the fourth position refers to multiparameter programmability. This means that three or more parameters can be programmed, but this code doesn't identify which parameters are capable of being adjusted. The letter "C" in the fourth position refers to communicating or telemetry. Generally, all pacemakers identified by the letter "C" have multiparameter programmability. The ability to communicate means that the pacemaker has the capability to transmit information concerning its function and how it is programmed to an external device, such as a programmer. The letter "R" in the fourth position indicates that the pacemaker has rate-modulation capability, namely its rate can be automatically adjusted in response to the input from a special detector or sensor that recognizes a signal other than the basic cardiac depolarization which is processed by the sensing circuit. All pacemakers with rate modulation capability have multiparameter programmability and communication ability.

The fifth position of the code refers to special and automatic antitachycardia functions. Again, a "O" in this position indicates that it does not have this capability. A "P" refers to the ability of the device to release one or more impulses in response to a fast heart rate, or tachycardia. This is termed antitachycardia pacing and uses energy levels in the range normally used by a pacemaker, i.e., microjoules. If an "S" is used in the fifth position, it indicates that the device can deliver a shock in an attempt to terminate or end a tachycardia. A shock is a large energy pulse delivering energy 1,000,000 times that of a standard pacemaker pulse. The unit of energy for a shock pulse is joules. A "D" in the fifth position means that the device is capable of dual modes of antitachycardia response.

Returning to the basic concept of a pacemaker for treating bradycardias, most current pacing devices are called demand units. This means that they are capable of sensing the electrical activity of the heart chamber by way of the pacing lead placed in or on that chamber. The electrical signal sensed inside or on the heart is called an electrogram (EGM). The EGM is a very rapid, relatively large signal. The most rapid portion of this signal is called the intrinsic deflection (ID). Although medical personnel commonly talk about pacemakers sensing P-waves or R-waves, this is not technically correct. The P-wave and R-wave are those portions of the surface ECG corresponding to atrial and ventricular depolarization, respectively. The pacemaker sensing circuits sense the atrial or ventricular intrinsic deflection portion of the atrial or ventricular EGM from within the heart. The atrial EGM coincides with the P-wave of the surface ECG, while the ventricular EGM coincides with the R-wave of the surface ECG. For purposes of this application, the terms "P-wave" and "R-wave" will be used synonymously with the atrial and ventricular electrograms.

One of the parameters of the pacemaker that can commonly be programmed or set by the physician is the base rate. This is the lowest rate that can occur in a patient before the pacemaker will release an output pulse to initiate a cardiac depolarization followed by a contraction. If the patient's intrinsic heart rate is faster than the base rate of the pacemaker, the pacemaker will recognize the native electrical depolarization and be either inhibited or triggered depending upon how it is set and reset in its various timing cycles in response to this sensed event. If the patient's own heart beat attempts to slow below the programmed base rate of the pacemaker, the pacemaker's timing circuits (or "timers") will cause the pacemaker to release an electrical impulse at the programmed base rate, thus preventing the patient's heart rate from falling below the programmed base rate.

The interval between consecutive pacing impulses within the same chamber is termed the automatic interval or basic pacing interval. The interval between a sensed event and the ensuing paced event is called an escape interval. In single chamber pacing systems, the automatic and escape intervals are commonly identical. In dual chamber pacing systems, the basic pacing interval is divided into two sub-intervals. The interval from a sensed R-wave or ventricular paced event to the atrial paced event is called an atrial escape interval. The interval from the sensed P-wave or atrial paced event to the ventricular paced event is called the AV interval.

In the majority of individuals, the most effective heart beat is caused by the patient's own intrinsic electrical activity. A pacemaker is intended to fill in when the patient's intrinsic rhythm fails. The first pacing mode that was developed was single chamber ventricular stimulation. It was soon recognized that this resulted in the loss of appropriate synchronization between the atria and ventricles, resulting in the efficiency of the heart being compromised and the cardiac output falling, despite maintaining an adequate rate.

In those patient's whose need for a pacemaker was intermittent, i.e., where the patients had a normal rhythm between the times when pacing support was required, pacemakers were developed which were initially set to a slow rate, which slow rate could could be subsequently programmed, as required. This allowed the patient's intrinsic rhythm to slow to this very low escape rate before the pacemaker would be activated. While the patient would be protected from asystole (a total absence of any heart beat), the loss of appropriate AV synchrony combined with the slow rate was often hemodynamically compromising.

Hence, an operating modality known as "hysteresis" was developed. With hysteresis, the escape rate of the pacemaker was slower than the automatic rate. This allowed the patient's normal rhythm to persist until the rate fell below the hysteresis escape rate. When this happened, there would be one cycle of pacing at the hysteresis escape rate followed by pacing at a more rapid rate until a native R-wave occurred and was sensed to again inhibit the pacemaker.

A number of problems were recognized with hysteresis. One was confusion on the part of the medical personnel caring for the patient because the patient's intrinsic rhythm was often running at a slower rate than the automatic rate of the pacemaker. The second was that a slow heart rate often caused premature ventricular contractions (PVCs) to occur. A PVC is essentially an R-wave that occurs out of sequence, i.e., consecutive R-waves without an intervening atrial depolarization. Because the PVC would be a sensed R-wave, its occurrence would reset the pacing system to the hysteresis escape rate following each PVC that occurred, effectively maintaining a slow rate.

Based upon these two drawbacks (confusion on the part of the medical community and the repeated resetting of the pacemaker by PVCs), hysteresis was not well accepted by the medical community until such time as it was introduced as a programmable parameter capable of being enabled or disabled, and if enabled, with the degree of hysteresis being adjustable.

Since the goal of hysteresis was to allow the patient to remain in a normal rhythm with appropriate AV synchrony as much time as possible while providing pacing support at an appropriate rate only at those times when the patient required this support, hysteresis was not incorporated in the first generation of dual chamber pacing systems because such systems were designed to always provide appropriate AV synchrony. However, some physicians recognized that some patients whose heart rate would precipitously and abruptly slow not only needed a more rapid rate at these times, they also required AV synchrony. These episodes were infrequent. If one were to program the base rate of the pacemaker to the rate which was required when pacing was needed, the pacemaker would be frequently controlling the patient's rhythm even when pacing was not needed. To address this concern, some of the first generation dual chamber pacemakers were programmed to provide hysteresis in the DDI mode. This allowed the pacemaker to remain inhibited during a normal rate, to turn on only when the pacemaker was needed as represented by a precipitous and dramatic slowing of the native rhythm but once activated, to then pace in both atrium and ventricle at a more rapid rate until such time as a native R-wave was sensed to return the pacemaker to the inhibited state requiring completion of another hysteresis escape interval before it would again release atrial and ventricular output pulses.

A couple of problems were recognized in this first application of hysteresis in the DDI mode. The first was that PVCs, a limitation first noted with single chamber hysteresis systems, proved equally limiting in the dual chamber pacing mode. The second was that while pacing was required, the patient's often needed a relatively short AV delay for optimum hemodynamic function. The short AV delay could result in the pacemaker usurping control of the normal conduction system resulting in sustained periods of pacing when it was no longer required. Thus, if a long AV delay were programmed which would result in appropriate pacing system inhibition when pacing therapy was not required, it also might allow intact AV conduction when pacing was required. Such AV conduction, which is manifest by the occurrence of an R-wave, could thus reinitiate the hysteresis escape interval, causing sustained pacing at the relatively slow hysteresis escape rate. While the relatively slow hysteresis escape rate might be appropriate for one cycle, it is certainly not appropriate for sustained periods of time when pacing therapy is required.

The present invention is intended to incorporate hysteresis in the dual chamber pacing mode, specifically the DDI mode, with unique designs which: (1) protect the pacemaker timers from being reset by a PVC during sustained periods of AV pacing; (2) allow for a long AV interval when the pacing system is inhibited; (3) provide for a shorter AV interval during AV pacing, but periodically screen or search for resumption of AV conduction during periods of pacing to determine if the pacemaker should again be inhibited.

SUMMARY OF THE INVENTION

The present invention addresses the above and other needs by providing a dual-chamber pacemaker that offers DDI pacing with PVC-protected hysteresis and automatic AV interval adjustment. As with conventional dual-chamber pacemakers, the dual-chamber pacemaker of the present invention includes an atrial channel and a ventricular channel. The atrial channel includes means for sensing P-waves, and means for generating atrial stimulation pulses (A-pulses). The ventricular channel similarly includes means for sensing R-waves, and means for generating ventricular stimulation pulses (V-pulses). The dual-chamber pacemaker further includes a control system that controls the atrial and ventricular channels so as to operate the pacemaker in a DDI mode of operation. In such DDI mode of operation, two time intervals are defined: an atrial escape interval (AEI), and an AV interval (AVI). The AEI begins upon the occurrence of ventricular activity, i.e., upon the occurrence of an R-wave, or upon the generation of a V-pulse. At the conclusion or "timing-out" of the AEI, the AVI begins. During the AVI, the ventricular channel determines if an R-wave occurs. If an R-wave is sensed prior to the timing-out of the AVI, then the AVI immediately ends, causing the next AEI to begin, and no V-pulse is generated. If the AVI times-out without an R-wave having been sensed, then a V-pulse is generated, and the next AEI begins. During the AEI, the atrial channel determines if a P-wave occurs. If the AEI times-out without a P-wave having been sensed, then an A-pulse is generated, and the next AVI begins. If a P-wave is sensed prior to the timing-out of the AEI, then no A-pulse is generated, but the AEI must still time-out before the AVI begins. Thus, in the DDI mode, the sensing of a P-wave in the atrial channel only inhibits the generation of an A-pulse, it does not start the AVI. In contrast, the sensing of an R-wave in the ventricular channel not only inhibits the generation of a V-pulse, but it also starts the AEI.

Unlike DDI pacemakers of the prior art, the present invention adds a PVC-protected hysteresis function to the DDI operation.. In accordance with such PVC-protected hysteresis function, the control system provides for one of two interval values to be used as the AEI. A first value, $AEI_1$, is used following the generation of a V-pulse in the ventricular channel. A second value, $AEI_H$, is a hysteresis escape interval value that is used following a PR event or an AR event. A PR event occurs when an R-wave is sensed in the ventricular channel following the sensing of a P-wave in the atrial channel. Similarly, an AR event occurs when an R-wave is sensed in the ventricular channel following the generation of an A-pulse in the atrial channel. Advantageously, by only using the longer $AEI_H$ as the atrial escape interval following a PR or an AR event, the occurrence of a premature ventricular contraction (PVC), which is an R-wave that is not preceded by an atrial paced or sensed event, does not trigger the longer $AEI_H$. Thus, the potentially undesirable effects of inserting a longer pause following a PVC are avoided.

In accordance with one aspect of the invention, the longer $AEI_H$ is not invoked unless a sensed AR or PR interval exceeds a prescribed reference interval, e.g., 100 msec, thereby further assuring the sensed R-wave has resulted from atrial conduction, i.e., that it represents the culmination of a true AR or PR event, and has not resulted from an ectopic beat. This condition is referred to as a "late cycle PVC", i.e., an R-wave that occurs shortly after the atrial paced or sensed event at an interval that is deemed too short to reflect intrinsic AV nodal conduction. Thus, the present invention provides DDI with PVC protection that does not invoke the longer $AEI_H$ in reponse to either a true PVC (a sensed R-wave that is not preceded by an atrial sensed or paced event) or a late cycle PVC (an R-wave that follows an atrial paced or sensed event but at an interval that is too short to reflect intrinsic AV nodal conduction).

In accordance with another aspect of the invention, the control system of the dual-chamber pacemaker further provides for the automatic adjustment of the AVI, and periodically searches for an optimum AVI. This is done to minimize the possibility of a long programmed AVI resulting in sustained functional AAI pacing at the hysteresis rate, which rate may be too slow to provide the patient the pacemaker support which the patient needs. In accordance with this aspect of the invention, one of two (or more) interval values are used for the AVI. A first value, $AVI_1$, is used as the AVI for so long as a P-wave is sensed during the timing-out of the longer hysteresis atrial escape interval, $AEI_H$. A second shorter value of the AVI, $AVI_2$, is automatically invoked following the delivery of an A-pulse upon the timing-out of the $AEI_H$ without having sensed a P-wave. The $AVI_2$ value is maintained for a programmed number n of cardiac cycles of DDI operation.

In accordance with yet another aspect of the invention, after operating the pacemaker in the DDI mode for the programmed number n of cardiac cycles using the shortened $AVI_2$ value, a search is performed to determine if the AVI should be returned to its initial programmed value. Such search is performed by temporarily lengthening the AVI, e.g., to a value equal to or associated with $AEI_1$, to determine if AV conduction is present. (AV conduction is manifest by the occurrence of an R-wave following atrial activity. The absence of AV conduction is manifest by the generation of a V-pulse following the AVI.) Such temporary lengthening of the AVI lasts for only a short time, e.g., for one or two cardiac cycles. If there is no AV conduction (i.e., if a V-pulse is generated due to the failure to sense an R-wave) while using the temporarily lengthened AVI, then the shortened AVI, $AVI_2$, is reinstated for a second number m of programmed cycles of DDI operation, where m may be equal to n. If there is AV conduction (i.e., if a PR or AR event occurs) while using the temporarily lengthened AVI, then the AVI is lengthened or returned to the $AVI_1$ value over a prescribed number of cardiac cycles. Such return to the $AVI_1$ value may occur abruptly, e.g., in one or two cardiac cycles, or smoothly, e.g, gradually over several cardiac cycles.

In accordance with an additional aspect of the invention, the pacemaker progressively slows the basic pacing rate at the same time that it temporarily lengthens the AVI while testing for AV conduction. That is, should AR pacing be recognized during the temporarily lengthened AVI, then the basic pacing rate is progressively slowed while maintaining the longer AVI. This action allows for AR pacing to occur at progressively slower rates until either the hysteresis escape rate, $AEI_H$, is again reached, or until a native P-wave is sensed, thus restoring control of the patient's rhythm to the patient.

It is thus a feature of the present invention to provide a hysteresis function in a dual-chamber pacemaker operating in the DDI mode.

It is an additional feature of the invention to provide such a DDI dual-chamber pacemaker wherein the hysteresis function (of extending the atrial escape interval in response to natural AV conduction) is not triggered by the occurrence of a premature ventricular contraction (PVC).

It is another feature of the invention to provide such a DDI dual-chamber pacemaker wherein the AV interval of the pacemaker is automatically adjusted in order to avoid sustained pacing at the hysteresis rate.

It is a further feature of the invention to provide such a DDI dual-chamber pacemaker wherein, after the AV interval has been adjusted, it automatically attempts to return to its initial value at an appropriate time, and does return to its initial value if prescribed conditions, e.g., AV conduction, are present.

It is yet another feature of the invention to provide a dual-chamber pacemaker, or method of operating such a dual-chamber pacemaker, that provides a PVC-protected DDI hysteresis mode that extends the atrial escape interval in response to a PR or an AR event. Further, it is a feature of such pacemaker, or method of operating the pacemaker, to also automatically shorten the AV interval in response to the generation of an A-pulse at the timing-out of the extended atrial escape interval (in order to minimize the possibility of sustained functional atrial rate pacing at the hysteresis rate); and to automatically return the AV interval to its original programmed value at an appropriate time thereafter.

BRIEF DESCRIPTION OF THE DRAWINGS

The above and other aspects, features and advantages of the present invention will be more apparent from the following more particular description thereof, presented in conjunction with the following drawings wherein:

FIG. 3 is a timing diagram that defines the basic time intervals associated with the operation of a dual-chamber pacemaker in the DDI mode;

FIG. 4 is a timing diagram that illustrates the DDI pacing mode used with hysteresis;

FIG. 5 is a further timing diagram that depicts how the occurrence of a PVC, absent the present invention, could extend the pacing interval to dangerously long intervals;

FIG. 6 is another timing diagram that shows how a long programmed AV interval could, absent the present invention, cause functional AR pacing at the long hysteresis escape interval;

FIG. 7 is a simplified flowchart that functionally illustrates DDI pacing with PVC-protected hysteresis in accordance with the present invention.

Corresponding reference characters indicate corresponding components or elements throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

As an overview, the present invention provides a dual-chamber implantable pacemaker that includes: (1) an atrial channel comprising an atrial pulse generator and an atrial sense amplifier; (2) a ventricular channel comprising a ventricular pulse generator and a ventricular sense amplifier; (3) timing means for defining an atrial escape interval (AEI) and an AV interval, with the AEI assuming one of at least two programmable values: a first value $AEI_1$ comprising a normal or programmed atrial escape interval, and a second value $AEI_H$ comprising a hysteresis atrial escape interval; and (4) a control circuit for controlling the atrial channel and the ventricular channel in accordance with a hysteresis DDI mode of operation.

The hysteresis DDI mode of operation, in accordance with the present invention, controls the operation of the dual-chamber pacemaker so that: (1) an atrial pulse (A-pulse) is generated by the atrial pulse generator at the termination of the AEI, unless an atrial event (P-wave) is sensed by the atrial sense amplifier during the AEI, in which case the A-pulse is inhibited from being generated; (2) a ventricular pulse (V-pulse) is generated by the ventricular pulse generator at the termination of the AV interval, unless a ventricular event (R-wave) is sensed by the ventricular sense amplifier during the AV interval, in which case the V-pulse is inhibited from being generated; (3) the AEI begins upon the occurrence of an R-wave or a V-pulse, with the AEI assuming the hysteresis $AEI_H$ value only upon the occurrence of: (a) an R-wave following a P-wave (a PR event), or (b) an R-wave following an A-pulse (an AR event), and with the AEI assuming the normal $AEI_1$ value at all other times; and (4) the AV interval begins following the AEI. In accordance with DDI operation, the consecutive occurrence of the AEI and the AV interval comprises a cardiac cycle, with sensing in the atrial channel (i.e., sensing a P-wave) only inhibiting the atrial channel output (an A-pulse), not starting the AV interval. The AV interval thus is only started upon the timing-out of the AEI.

Figure 1:
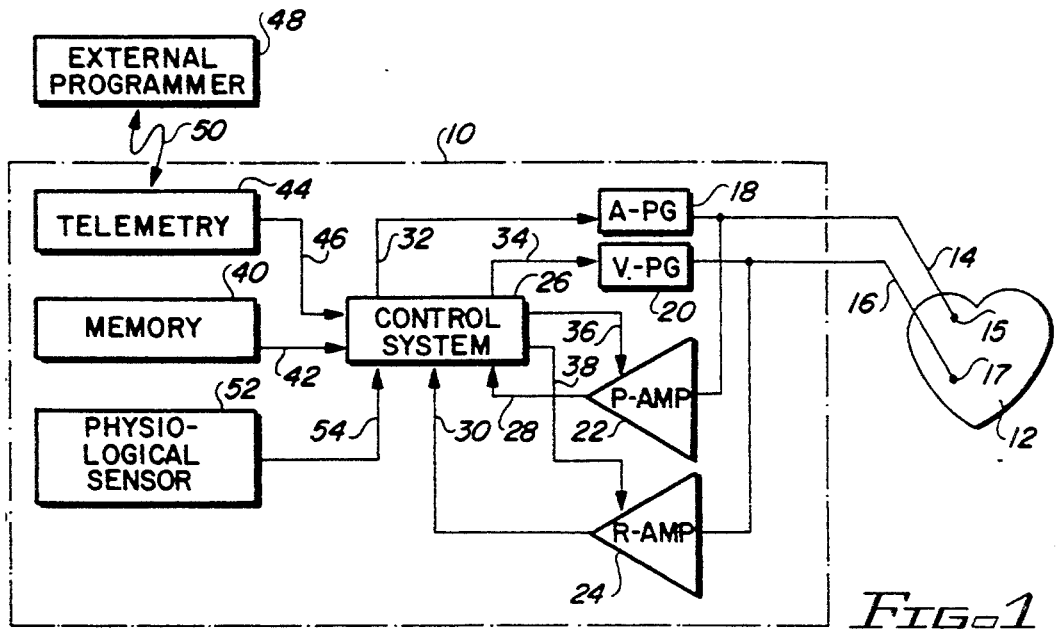
FIG. 1 is block diagram of a dual-chamber programmable pacemaker.

A simplified functional block diagram of a dual-chamber pacemaker 10 made in accordance with the present invention is shown in FIG. 1. When implanted (or otherwise operatively connected to a patient), the pacemaker 10 is coupled to a heart 12 by way of leads 14 and 16, the lead 14 having an electrode 15 that is in contact with one of the atria of the heart, and the lead 16 having an electrode 17 that is in contact with one of the ventricles of the heart. The leads 14 and 16 carry stimulating pulses to the electrodes 15 and 17 from an atrial pulse generator (A-PG) 18 and a ventricular pulse generator (V-PG) 20, respectively. Further, electrical signals from the atria are carried from the electrode 15, through the lead 14, to the input terminal of an atrial channel sense amplifier (P-AMP) 22; and electrical signals from the ventricles are carried from the electrode 17, through the lead 16, to the input terminal of a ventricular sense channel amplifier (R-AMP) 24.

Controlling the dual-chamber pacer 10 is a timing-/control system 26. The timing/control system 26 (referred to hereafter as simply the control system 26) receives the output signals from the atrial amplifier 22 over signal line 28. Similarly, the control system 26 receives the output signals from the ventricular amplifier 24 over signal line 30. The output signals on signal lines 28 and 30 are generated each time that a P-wave or an R-wave is sensed within the heart 12. The control system 26 also generates trigger signals that are sent to the atrial pulse generator 18 and the ventricular pulse generator 20 over signal lines 32 and 34, respectively. These trigger signals are generated each time that a stimulation pulse is to be generated by the respective pulse generator 18 or 20. The atrial trigger signal is referred to simply as the "A-pulse," and the ventricular trigger signal is referred to as the "V-pulse." During the time that either an A-pulse or V-pulse is being delivered to the heart, the corresponding amplifier, P-AMP 22 and/or R-AMP 24, is typically disabled by way of a blanking signal presented to these amplifiers from the control system over signal lines 36 and 38, respectively. This blanking action prevents the amplifiers 22 and 24 from becoming saturated from the relatively large stimulation pulses that are present at their input terminals during this time. This blanking action also helps prevent residual electrical signals present in the muscle tissue as a result of the pacer stimulation from being interpreted as P-waves or R-waves.

Still referring to FIG. 1, the pacer 10 also includes a memory circuit 40 that is coupled to the control system 26 over a suitable data/address bus 42. This memory circuit allows certain control parameters used by the control system 26 in controlling the operation of the pacemaker to be programmably stored and modified, as required, in order to customize the pacer's operation to suit the needs of a particular patient. Such control parameters include the basic timing intervals used during operation of the pacemaker, such as the programmed atrial escape interval ($AEI_1$), the programmed AV interval ($AVI_1$), as well as the amount that $AEI_1$ is to change because of the hysteresis provided by the present invention, or the amount that the AV interval $AVI_1$ is to change when shortened in accordance with the present invention (explained below). In some embodiments of the pacemaker 10, a full set of timing control parameters, such as $AEI_1$, $AEI_H$, $AVI_1$, $AVI_2$, are programmably stored in the memory circuit 40 and retrieved at the appropriate time for use by the control system 26. In other embodiments of the pacemaker 10, a basic atrial escape interval, AEI, and a basic AV interval, AVI, are programmed into the memory circuit 40, along with appropriate parameters that define how much the basic AEI and AVI are to change as the invention is carried out. The control system 26 then retrieves the basic AEI and AVI and related parameters, stored in the memory 40 at the appropriate time and processes them in order to derive or otherwise define the desired time intervals and other control parameters needed as the invention is carried out. Further, in some embodiments of the invention, signals sensed during the operation of the pacemaker 10 may be stored in the memory 40 as data signals for later retrieval and analysis. Such data may include operating parameters associated with the pacemaker, such as the battery voltage or lead impedance, and/or cardiac signals sensed during operation of the pacemaker, such as the EGM signals.

A telemetry circuit 44 is further included in the pacemaker 10. This telemetry circuit 44 is connected to the control system 26 by way of a suitable command/data bus 46. In turn, the telemetry circuit 44, which is included within the implantable pacer 10, may be selectively coupled to an external programmer 48 by means of an appropriate communication link 50, which communication link 50 may be any suitable electromagnetic link, such as inductive coupling or an rf channel. Advantageously, through the external programmer 48 and the communication link 50, desired commands and control parameters may be sent to the control system 26. Similarly, in some pacemaker embodiments, data signals (either held within the control system 26, as in a data latch, or stored within the memory 40) may be remotely received through the communication link 50 and the programmer 48. In this manner, non-invasive communications can be established with the implanted pacer 10 from a remote, non-implanted, location.

The pacemaker 10 in FIG. 1 is referred to as a dual-chamber pacemaker because it interfaces with both the atria and the ventricles of the heart. Those portions of the pacer 10 that interface with the atria, e.g., the lead 14, the P-wave sense amplifier 22, the A-pulse generator 18, and corresponding portions of the control system 26, are commonly referred to as the atrial channel. Similarly, those portions of the pacer 10 that interface with the ventricles, e.g., the lead 16, the R-wave sense amplifier 24, the V-pulse generator 20, and corresponding portions of the control system 26, are commonly referred to as the ventricular channel.

In accordance with some embodiments of the present invention, the pacemaker 10 may further include at least one physiological sensor 52 that is connected to the control system 26 of the pacemaker over a suitable connection line 54. While this sensor 52 is illustrated in FIG. 1 as being included within the pacer 10, it is to be understood that the sensor may also be external to the pacer 10, yet still be implanted within or carried by the patient. A common type of sensor is an activity sensor, such as a piezoelectric crystal, mounted to the case of the pacemaker. Other types of physiologic sensors are also known, such as sensors that sense the oxygen content of blood, respiration rate, pH of blood, body motion, and the like. The type of sensor used is not critical, as any sensor capable of sensing some physiologic-related parameter that indicates or suggests the rate at which the heart should be beating can be used. Such sensors are commonly used with "rate-responsive" pacemakers in order to adjust the rate (typically by adjusting the length of the atrial escape interval) of the pacer in a manner that tracks the physiological needs of the patient.

Figure 2:
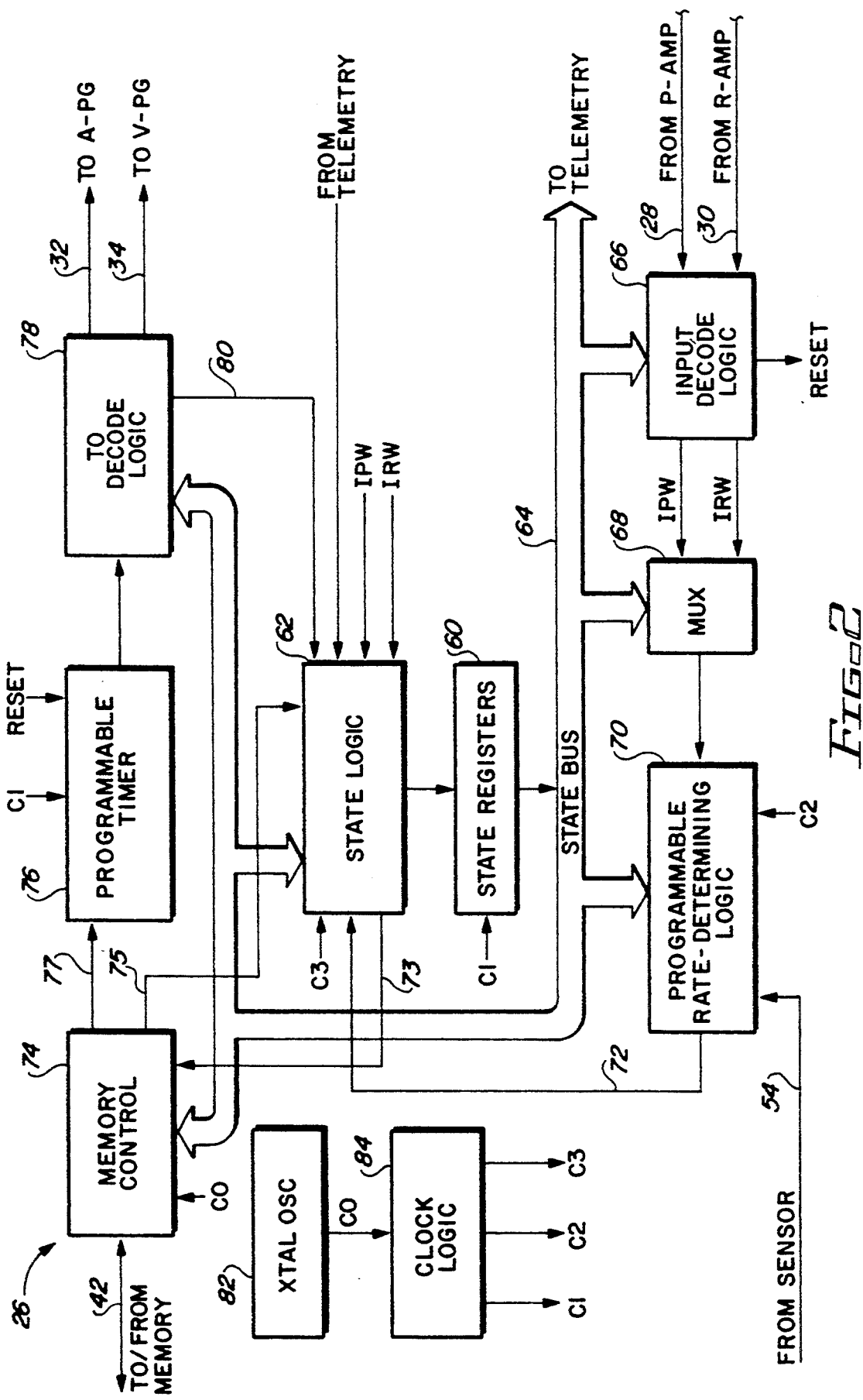
FIG. 2 is a block diagram of one possible embodiment of the control logic of the pacemaker of FIG. 1.

Referring next to FIG. 2, a block diagram of one embodiment of the control system 26 of the pacer 10 is illustrated. It is noted that other embodiments of a control system 26 may also be utilized, such as a microprocessor-based control system. A representative microprocessor-based system is described, for example, in U.S. Pat. No. 4,940,052, entitled "Microprocessor Controlled Rate-Responsive Pacemaker Having Automatic Threshold Adjustment." The '052 patent is assigned to the same assignee as is this application, and is incorporated herein by reference.

The control system shown in FIG. 2 is based on a state machine wherein a set of state registers 60 define the particular state of the pacer at any instant in time. In general, and as an overview of state machine operation, each state, by design, causes a certain activity or function to be carried out. Several states are executed in a sequence during a given cardiac cycle. The sequence of states that is executed in a particular cardiac cycle is determined by the particular events that occur, such as the sensing of a P-wave or an R-wave, as well as the current state, as certain states can only be entered from certain other states. Only one state can exist at any instant of time, although several different state machines (or control systems) may operate in parallel to control diverse functions. For example, the telemetry circuit 44 (FIG. 1) preferably utilizes its own state machine, such as is described in the above-cited patent. This telemetry circuit state machine operates essentially independent of the control system state machine of FIG. 2.

At the heart of the control system 26 is the state logic 62. It is the state logic that controls the "state" of the state registers 60, and hence the function or operation that will next be carried out by the system. The state logic 62 receives as inputs the current state of the state registers, made available over a state bus 64 (which state bus directs the state of the system to several sections of the control system), as well as other signals indicating the current status of the system or events that have occurred. The output signals from the P-AMP 22 (FIG. 1) and the R-AMP 24 (FIG. 1) are directed to an input decode logic circuit 66. This circuit generates appropriate logic signals "IPW" (Inhibiting P-Wave) and "IRW" (Inhibiting R-Wave) that are selected by a multiplexer 68 and sent to rate-determining logic 70. These signals are also sent to the state logic 62. The function of the rate-determining logic 70 is to determine the rate at which either the IPW or IRW signals are occurring. A signal representative of this rate is sent, as an output signal from the rate determining logic 70, to the state logic 62 over signal line 72. Rate-determining logic 70 further receives a sensor rate signal from the sensor 52 (FIG. 1), and (depending upon the particular state of the system, as defined by the state registers 60, and as made available to the rate-determining logic 70 over the state bus 64) sends a rate signal to the state logic 62 over signal line 72 indicative of this sensor rate.

Still referring to FIG. 2, a memory control circuit 74 provides the needed interface between the circuits of the control system 26 and the memory 40 (FIG. 1). This memory control circuit may be any conventional memory access circuit that sends or receives data signals to or from memory at a specified address. Data signals retrieved from memory 40 may be sent to either the state logic 62 (over signal line(s) 75) or to a programmable timer 76 (over signal line(s) 77). Data signals sent to memory 40 may be either the current state of the system (obtained off of the state bus 64), or other selected signals from the state logic (as made available over signal line(s) 78).

The programmable timer 76 defines a prescribed time interval, the length of which is set by the signal(s) received from the memory control 74 over signal line(s) 77, and the starting point of which begins coincident with the start of the current state, as obtained from the state bus 64. The timer 76 further generates a time-out (T.O.) signal when this prescribed time interval has elapsed. During this prescribed time interval, the timing function may be reset by a reset signal, typically obtained from the input decode logic 66, although some states (as obtained from the state bus 64) may also effectuate an immediate reset of the timer 76. The time-out signal is sent to time-out decode logic 78. It is the function of the time-out decode logic to generate the appropriate trigger signals that are sent to the A-pulse generator 18 or the V-pulse generator 20 (FIG. 1). Further, an appropriate logic signal(s) is sent to the state logic 62 by the time-out decode logic 78 over signal line(s) 80 in order to notify the state logic that the respective time-out signals have occurred and/or that the respective trigger signals have been generated.

An oscillator 82, preferably a crystal-controlled oscillator, generates a basic clock signal C0 that controls the operation of the system logic. This clock signal C0 is sent to clock logic circuits 84, where other appropriate clock signals, such as clock signals C1, C2 and C3, are generated, all derived from the basic clock signal C0. These clock signals are distributed throughout the control system 26 in order to appropriately synchronize the various events and state changes that occur within the pacemaker. The rate of the basic clock signal C0 is not critical to the present invention. In general, a rate of 25–40 Khz for the basic clock rate C0 is adequate. This rate provides a basic time increment of 25–40 microseconds each clock cycle, and this is more than enough time to effectively control the pacemaker operation. If desired, a faster basic clock rate can be used, particularly by the memory control 74, to speed up the data transfer between the control system 26 and the memory 40, although for most pacemaker operations, a fast data transfer rate is not essential.

In operation, the control system of FIG. 2 starts at an initial state, wherein the state registers 60 assume a prescribed value that defines the initial state. For example, assuming four flip flops are used for the state registers 60, an initial state might be "1000" (hexadecimal "8") wherein the first flip flop assumes a "1" state, and the remaining three flip flops each assume a "0" state. This state may be defined as a V-A Delay (VAD) state wherein a prescribed ventricular-to-atrial (V-A) interval is initiated. This VA interval may be considered as the "atrial escape interval," or "AEI." As soon as the memory control 74 detects that the VAD state has been initiated, as evidenced by the "1000" appearing on the state bus 64, it retrieves from the memory 40 an appropriate data word, previously programmed into the memory 40 from the external programmer 48, or stored in the memory by the state logic 62, that defines the desired length of the AEI. In accordance with the present invention, this defined length is normally a value $AEI_1$, although for some cardiac cycles it may be extended to a hysteresis value, $AEI_H$, as explained below. The appropriate data word is sent to the programmable timer 76 and sets the length of the time period that is to be measured during the VAD state.

The timer 76 is essentially just a counter that counts down (or counts up), using a specified clock signal, to the value specified in the retrieved data word. When the counting has been completed, the counter or timer 76 is said to have "timed-out," and an appropriate time-out signal is generated that is sent to the time-out decode logic 78. Note that in the DDI mode, the AEI will always time-out, regardless of whether a P-wave occurs during the timing-out of the AEI. That is, it is a characteristic of the DDI mode to not begin the AV interval until the AEI times-out. If a P-wave is sensed during the AEI, such sensing inhibits the generation of an A-pulse at the conclusion of the AEI, but it does not reset the AEI. This is in contrast to other pacing modes, wherein the occurrence of a P-wave during the AEI may immediately reset the counter that defines the AEI. The decode logic, in turn, recognizes that the current state of the system is the VAD state (as determined by monitoring the state bus 64), and therefore that the AEI has timed-out. If a P-wave was sensed during the timing-out of the AEI, then an appropriate flag is set that inhibits the generation of the trigger signal that would otherwise trigger the A-PG 18 (FIG. 1) to generate an A-pulse at the end of the AEI. If a P-wave was not sensed during the timing-out of the AEI, then such flag is not set, and an appropriate A-pulse trigger signal is generated and sent to the A-PG 18 at the conclusion of the AEI, thereby causing an A-pulse to be generated so that the atrium can be stimulated. At the same time, an appropriate logic signal(s) is sent to the state logic 62 over the signal line(s) 80 to alert the state logic to the fact that the timer 76 has timed-out.

The state logic 62, in response to receiving the signal(s) from the time-out decode logic 78, and also in response to the current VAD state, triggers the next state of the prescribed sequence. For DDI operation, this state is typically a blanking state, or BLANK state, during which the P and R sense amplifiers, 22 and 24, are disabled. Accordingly, the state logic generates appropriate signal(s) on signal lines 36 and 38 to blank the P-wave sense amplifier 22 and the R-wave sense amplifier 24, and also causes the state registers 60 to change to a BLANK state, which state could be defined, for example, by the flip flops of the state registers 62 assuming a "0001" (hex "1") condition. This BLANK state, detected on the state bus 64, causes the memory control circuitry to retrieve an appropriate data word from memory that defines the length of the blanking interval, which data word is loaded into the programmable timer 76. As soon as the timer 76 times-out, indicating that the prescribed blanking interval has elapsed, a time-out signal is generated that is sent to the time-out decode logic 78. Upon receipt of this time-out signal, and in response to the current state being a BLANK state, the time-out decode logic 78 sends an appropriate logic signal to the state logic 62. The state logic 62 responds by steering the state registers 62 to assume the next state in the prescribed sequence, which may be, for example, a VA interval state.

At the beginning of the VA interval state, another value is loaded into the programmable timer 76 that defines the length of the VA interval, or VAI. If the timer 76 times-out without being reset, indicating that no R-wave has been sensed, the decode logic generates a V-pulse trigger signal, and notifies the state logic 62 of this event. If the timer 76 is reset, indicating that an R-wave was sensed, then the generation of a V-pulse is inhibited, and notifies the state logic 62 of this event. The state logic, in turn, causes the next appropriate state to be entered, which state may be another blanking state, or BLANK state, similar to the one described above, but having perhaps a different duration, or it may be a refractory (REF) state. At the conclusion or timing-out of the BLANK and/or REF state (typically, a REF state follows a BLANK state when a V-pulse is generated; but if an R-wave is sensed, the BLANK state may, in some embodiments, be skipped), the next state in the prescribed sequence is initiated, which state may again be the VAD state.

In the manner described above, the control system 26 assumes one state after another, thereby controlling the operation of the pacemaker. In general, a state is changed when the timer 76 times-out, or when a prescribed event occurs. For DDI operation, the two main timing intervals (and thus the two main states) that are invoked each pacing cycle are the VAD state (which applies the AEI) and the AV interval state (which applies the VAI). The AEI will always time-out in a DDI mode; whereas the AVI may be reset, immediately starting the next AEI, upon the occurrence of an R-wave. In accordance with the present invention, if a prescribed event occurs, e.g., the occurrence of a PR event or an AR event, the value of the pacer's programmed atrial escape interval, $AEI_1$, is lengthened to a new value, $AEI_H$. The longer atrial escape interval, $AEI_H$, is used for so long as PR or AR events continue to occur. Thus, upon the occurrence of a V-pulse, at the conclusion of the AV interval during which an R-wave was not sensed, the next atrial escape interval is changed back to the programmed value of $AEI_1$.

It is noted that the state of the control system may also be changed by receipt of an appropriate command from the telemetry system.

The control system 26 of FIG. 2 may be realized using dedicated hardware circuits, or by using a combination of hardware and software (or firmware) circuits. The appropriate sequence of states for a given mode of operation, such as DDI, for example, can be defined by appropriate control of the memory control 74 and the state logic 62. These circuit elements, in turn, are most easily controlled through an appropriate software or firmware program that is placed or programmed into the pacemaker memory circuits. The manner of accomplishing such programming is known in the art.

A detailed description of the various circuits of the control system 26 of FIG. 2 will not be presented herein because all such circuits may be conventional, or may be patterned after known circuits available in the art. Reference is made, for example, to U.S. Pat. No. 4,712,555 wherein a state-machine type of operation for a pacemaker is described; U.S. Pat. No. 4,788,980, wherein the various timing intervals used within the pacemaker and their interrelationship are more thoroughly described; and U.S. Pat. No. 4,944,298 wherein an atrial rate based programmable pacemaker is described, including a thorough description of the operation of the state logic used to control such a pacemaker. The '555; '980; and '298 patents are incorporated herein by reference.

Referring next to FIG. 3, a timing diagram is shown that defines the basic time intervals associated with the operation of a dual-chamber pacemaker in a DDI mode. Such timing diagram schematically shows a representation of the electrogram (EGM) signal that comprises the combination of events that are sensed or generated in the atrial and ventricular channels as a function of time. Also shown in FIG. 3, below the EGM representation, are the two primary timing intervals used for DDI pacing: the atrial escape interval (AEI), and the AV interval (AVI). Such timing intervals are represented as a horizontal line or arrow that points from left to right (the direction of increasing time). An arrowhead on the timing interval line represents the timing-out of the interval. A dot on the timing interval line represents that the interval was terminated due to the sensing of ventricular activity prior to the timing-out of the interval. In the case of the AEI, which is not reset in DDI operation, the remaining portion of the interval following sensed atrial activity, i.e., a P-wave, is shown as a dashed line. This is done to emphasize that the sensing of a P-wave is a significant event (because such sensing inhibits the generation of an A-pulse), but it does not alter the AEI timing. That is, the AEI must still time-out before the next AVI begins. Not shown in FIG. 3, or in any of the other timing diagrams presented in the other figures, are the blanking or refractory intervals, which may comprises part of the AEI or AVI.

As shown in FIG. 3, an R-wave 102 first occurs, which R-wave starts the timing-out of a corresponding AEI 103. A representative time increment for the AEI may be from 100 to 1400 msec. Before the AEI 103 times-out, at time t1, a P-wave 104 occurs. The occurrence of such P-wave inhibits the generation of an A-pulse, but it does not reset the AEI or otherwise prevent the AEI 103 from timing-out. As soon as the AEI 103 times-out, at time t2, an AVI 105 begins. A representative time increment for the AVI may be from 50 to 250 msec. No R-waves occur during the timing-out of the AVI 105. Thus, upon the timing-out of the AVI at time t3, a V-pulse 106 is generated. The occurrence of the V-pulse 106 following the P-wave 104 is referred to as a PV event 108. The PV event 108 commences with the P-wave 104, and culminates with the generation of the V-pulse 106.

The generation of the V-pulse 106 causes the ventricles to depolarize, which depolarization is represented in the EGM of FIG. 3 as the inverted R-wave 107. The V-pulse 106 further triggers the beginning of the next AEI 109. The AEI 109 times-out at time t4 without a P-wave having been sensed in the atrial channel. Thus, an A-pulse 108 is generated at time t4, causing the atria to depolarize, which depolarization is represented by the inverted P-wave 110. The timing-out of the AEI, as always, starts the beginning of the next AVI 111, which AVI times-out at time t5. As no R-wave occurred during the AVI 111, a V-pulse 112 is generated in the ventricular channel. The occurrence of the V-pulse 112 following the A-pulse 108 is referred to as an AV event 114. The AV event 114 thus commences with the A-pulse 108 and culminates with the generation of the V-pulse 112.

Still referring to the DDI operation depicted in FIG. 3, the V-pulse 112 triggers the beginning of the next AEI 113 at time t5. During the timing-out of the AEI 113, at time t6, a P-wave 114 is sensed in the atrial channel. The occurrence of the P-wave 114 inhibits the generation of an A-pulse, but does not reset the AEI 113. Thus, when the AEI 113 times-out, at time t7, the next AVI 115 begins. Before the AVI 115 times-out, at time t8, an R-wave 116 is sensed in the ventricular channel. The occurrence of the R-wave 116 causes the AVI 115 to be reset, and causes the next AEI 117 to begin. The occurrence of the P-wave 114 followed by the R-wave 116 is referred to as a PR event 118. The PR event 118 thus commences at time t6 and ends at time t8. The time interval between the times t6 and t8 may thus be referred to as the PR time interval. In accordance with one embodiment of the present invention, as explained more fully below, the PR time interval is measured and compared to a reference time interval, with the hysteresis function of the invention being invoked only if the PR time interval exceeds the reference time interval.

Continuing with the description of FIG. 3, the R-wave 116 causes the AVI 117 to terminate, which also causes the next AEI 117 to begin, at time t8. The AEI 117 times-out at time t9 without a P-wave having been sensed. Thus, an A-pulse 118 is generated by the atrial channel at time t9. The timing-out of the AEI 117 also causes the next AVI 119 to begin. Before the AVI 119 times-out, an R-wave 120 is sensed at time t10, causing the AVI 119 to immediately terminate, and the next AEI 121 to begin. The occurrence of the A-pulse 118 followed by the R-wave 120 is referred to herein as an AR event 122. As explained below, the time interval between the A-pulse and the R-wave of an AR event, i.e., the time interval between the times t9 and t10, comprises an AR time interval that may be measured by the present invention to determine the appropriateness of invoking a hysteresis AEI.

As seen in FIG. 3, there are thus four main events that typically occur during each cardiac cycle of DDI operation: a PV event, an AV event, a PR event or an AR event. To these basic four events, however, other events may also sometimes occur, such as a premature ventricular contraction (PVC), which is essentially two consecutive R-waves, or an R-wave following a V-pulse, without an intervening atrial event; or a late cycle PVC, which is essentially a PR or AR event that occurs in an interval that is deemed too short to reflect intrinsic AV nodal conduction.

Referring next to FIG. 4, a timing diagram is shown that illustrates a DDI pacing mode with hysteresis that is provided by the pacemaker 10 (FIG. 1) in accordance with the present invention. Such DDI hysteresis mode provides that one of two values for the AEI be used depending upon the particular events that precede the AEI. If a PR or AR event precedes the AEI, the AEI is extended to a hysteresis value, $AEI_H$. For any other event that precedes the AEI, e.g., an AV event, a PV event, or a PVC, the AEI remains at its programmed value, $AEI_1$. Hence, as seen in FIG. 4, an R-wave 130 occurs, which R-wave follows an A-pulse or a P-wave, not shown. The R-wave 130 thus represents the culmination of a PR event or an AR event, and causes the next AEI 132 to assume the extended hysteresis AEI value, $AEI_H$. The difference between $AEI_1$ and $AEI_H$ is a programmable value, and will typically fall within the range of 0 to 300 msec.

For the particular EGM shown in FIG. 4, a P-wave 134 occurs before the AEI 132 times-out. However, pursuant to classical DDI operation, such P-wave does not reset the AEI 132. Rather, the AEI 132 times-out, and starts the next AVI 136. The AVI 136 does time-out without an R-wave being sensed. Thus, at the conclusion (or timing-out) of the AVI 136, a V-pulse 138 is generated. The occurrence of the V-pulse 138 triggers the next AEI 140, which AEI 140 reverts back to its programmed value, $AEI_1$, because it does not follow a PR or AR event. The AEI 140 (of duration $AEI_1$), times-out without a P-wave being sensed, and hence an A-pulse 142 is generated. The timing-out of the AEI 140 also triggers the beginning of the next AVI 144. Again, for the particular EGM shown in FIG. 4, the AVI 144 times-out without an R-wave having been sensed. Thus, a V-pulse 146 is generated, and the next AEI 148 begins. The V-pulse 146 does not represent the culmination of either a PR or AR event, so the next AEI 148 thus assumes the normal programmed value, $AEI_1$.

Still referring to FIG. 4, the AEI 148 times-out without a P-wave having been sensed, thereby causing an A-pulse 150 to be generated. The timing-out of the AEI 148 also causes the next AVI 152 to begin. Prior to the timing-out of the AVI 152, an R-wave 154 is sensed in the ventricular channel. Such sensing causes the AVI 152 to immediately reset, and causes the next AEI 156 to begin. The AEI 156, because it follows an AR event (the A-pulse 150 followed by the R-wave 154) assumes the hysteresis value, $AEI_H$. Such hysteresis value provides a little longer time for the heart to beat on its own prior to stepping in with a stimulation pulse. For the EGM shown in FIG. 4, a P-wave 158 occurs before the timing-out of the AEI 156. However, pursuant to the DDI mode, the next AVI 160 does not begin until the AEI 156 times-out. Before the AVI 160 times-out, another R-wave 162 occurs, which R-wave 162 represents the culmination of a PR event (the P-wave 158 followed by the R-wave 162). Hence, the next AEI, which begins as soon as the AVI 160 is reset, also assumes the hysteresis $AEI_H$ value.

In the manner shown in FIG. 4, then, the hysteresis DDI mode of the present invention provides an extended atrial escape interval, $AEI_H$, following a PR or an AR event, and provides the basic programmed atrial escape interval, $AEI_1$, following any events other than a PR or AR event, e.g., a PV, AV or PVC event.

In one variation of the present invention, a feature is provided where not only is the extended hysteresis atrial escape interval, $AEI_H$, invoked only upon the occurrence of a PR or an AR event, but the time interval separating the atrial and ventricular events of such PR or AR event must exceed a prescribed reference value. Otherwise, the sensed PR or AR event may actually be what is known as a late cycle PVC. Such time interval is shown in FIG. 4 as the "AR interval" 153 and the "PR interval" 159. (Note: typically the PR interval will be somewhat shorter than the AR interval due to the latency associated with providing an external A-pulse to stimulate the atria.) Thus, in accordance with this feature of the invention, the AR interval 153 must exceed a prescribed reference interval value, e.g., 90–110 msec., before the $AEI_H$ 156 is triggered. Similarly, the PR interval 159 must exceed a prescribed reference interval value, e.g., 80–100 msec, before triggering the $AEI_H$. Such reference interval values for the PR and AR intervals are preferably set through conventional programming techniques when the operating parameters of the pacemaker are initially set.

The above-described feature (of not triggering the $AEI_H$ if the PR or AR intervals are too short) advantageously prevents the triggering of the extended atrial escape interval by a late cycle PVC, i.e., an R-wave that is not conducted from the atrium, but may have resulted, e.g., from a late cycle ventricular ectopic beat.

One of the advantages of the DDI hysteresis mode provided by the invention is that it is not triggered by the occurrence of a premature ventricular contraction (PVC). FIG. 5 shows what could happen, absent the present invention, if conventional hysteresis were employed in a DDI mode of operation. In a conventional hysteresis mode, the longer atrial escape interval is invoked upon the occurrence of natural ventricular activity, i.e., an R-wave. Thus, as seen in FIG. 5, an R-wave 170 triggers an extended atrial escape interval $AEI_H$ 172. However, before the $AEI_H$ 172 times-out, a PVC 174 occurs. The PVC 174 causes the AEI to reset and start over again. Thus, the PVC 174 triggers another atrial escape interval $AEI_H$ 176. The $AEI_H$ 176 times-out, as per DDI operation, invoking an A-pulse 178 to be generated (because no P-waves were sensed during the timing-out of the $AEI_H$. The timing-out of the $AEI_H$ 176 also causes the AVI 180 to start. Before the AVI 180 times-out, an R-wave 182 is sensed, causing the next $AEI_H$ 184 to start. However, before the $AEI_H$ 184 times-out, another PVC 186 occurs, causing the $AEI_H$ 184 to be reset, and a new $AEI_H$ 188 to begin. The $AEI_H$ 188 times-out, causing an A-pulse 190 to be generated in the atrial channel, and also causing the next AVI 192 to start. This cycle continues to repeat, with a PVC always retriggering the $AEI_H$, thereby forcing a pacing cycle that is longer than intended, and which may be much too slow to be of benefit for a given patient. With the present invention, however, the $AEI_H$ can only be invoked following the occurrence of either a PR or an AR event. Thus, the occurrence of a PVC does not reset the hysteresis escape interval timing, and the difficulty shown in FIG. 5 is avoided.

Another feature provided by the present invention is the automatic adjustment of the AV interval, AVI, following the occurrence of atrial pacing after the hysteresis atrial escape interval, i.e., following an A-pulse generated at the conclusion of $AEI_H$. The advantage of such automatic AVI adjustment feature is best evident from considering what could happen using DDI hysteresis absent such feature. Thus, with reference to FIG. 6, a timing waveform diagram is shown that illustrates DDI pacing absent the automatic AVI adjustment feature of the present invention. As seen in FIG. 6, an R-wave 200 (which is presumed to be the culmination of either an AR or a PR event) triggers the extended hysteresis atrial escape interval, $AEI_H$, 202. Because no P-wave is sensed during the timing-out of the $AEI_H$ 202, an A-pulse 204 is generated upon the timing-out of the $AEI_H$ 202. Also, at the timing-out of a the $AEI_H$ 202, the AVI 206 is started.

Should the AVI 206 be programmed to a value that is longer than the natural AV conduction time for the patient, then an R-wave will most always occur prior to the timing-out of the AVI. Such a condition is shown in FIG. 6. That is, in FIG. 6, it is assumed that the programmed value of AVI which may be considered as $AVI_1$, is somewhat longer than the natural AV conduction time of the patient. (The "natural AV conduction time" is the time it takes the R-wave stimulus to conduct to the ventricles from the atrium. Normally, the occurrence of AV conduction is manifest by the occurrence of an R-wave.) As seen in FIG. 6, the AVI 206 starts after the $AEI_H$ 202 times-out, as per DDI operation. However, before the AVI 206 times-out, an R-wave 208 occurs, as would be expected for a long AVI. The R-wave 208, representing the culmination of an AR event, triggers the next hysteresis atrial escape interval, the $AEI_H$ 210. Upon the timing-out of the $AEI_H$ 210, another A-pulse 212 is generated and the next AVI 214 begins. Before the AVI 214 times-out, another R-wave 216 occurs, which R-wave 216 represents the culmination of another AR event, thereby causing the next AEI 218 to assume the extended $AEI_H$ value. This process continues each cardiac cycle, that is, the $AEI_H$ times-out, an A-pulse is generated, followed by an R-wave before the timing-out of the AVI, thereby causing the atrial escape interval to always assume the $AEI_H$ value.

The continual repetition of the AR events as shown in FIG. 6 is referred to as sustained functional AAI pacing. Sustained functional AAI pacing may not be desirable in many instances because the effective pacing rate, which is primarily dictated by the extended atrial escape interval $AEI_H$, may be too long for the patient's needs at a time when the atrium is always being paced.

To overcome the disadvantage of sustained functional atrial pacing as shown in FIG. 6, the present invention includes an automatic AV interval adjustment feature. In accordance with such feature, the AV interval is automatically shortened, e.g., from its programmed value $AVI_1$ to a shortened value $AVI_2$, upon the occurrence of an A-pulse following the extended hysteresis atrial escape interval $AEI_H$. Shortening the AV interval in this manner effectively forces ventricular stimulation, i.e., the generation of V-pulses in the ventricular channel, thereby invoking the programmed atrial escape interval, $AEI_1$, and allowing the patient's heart an opportunity to break out of sustained functional atrial pacing.

A potentially adverse consequence of using the shortened AV interval is that sustained but "no longer necessary" pacing may then result from the faster rate and short AV interval. Such might occur, for example, if the pacing rate (set by the shortened AV interval and programmed atrial escape interval) is faster than the endogenous sinus rate (the patient's natural heart rate) after the cause of the intermittent slow heart rate has resolved itself. That is, after a time, the natural conduction time may no longer be less than the programmed AV interval, $AVI_1$. Thus, an additional feature of the invention is that periodically (e.g., after a preset number of cardiac cycles or a programmed number of cardiac cycles), the pacemaker performs a "search" to determine if the AV interval can appropriately be lengthened to the programmed AV interval, $AVI_1$.

Such "searching," or readjustment of the AV interval, is preferably performed as follows: the shortened AV interval value, $AVI_2$, is used only during the next n DDI pacing cycles, where n is an integer ranging from 2 to 30. (The number n may be a fixed number, or preferably it is programmed into the pacemaker by the physician at the time of implant, or thereafter.) After the n cardiac cycles of DDI pacing have been completed, a test is made to determine if AV conduction is present using a longer AV interval. Thus, in such test, the AV interval is momentarily or temporarily lengthened, e.g., to the programmed value $AVI_1$, for one or two cardiac cycles. Typically, the temporary AV interval will simply be the programmed AV interval, $AVI_1$. If an R-wave results when using such temporary value of the AV interval, then that is an indication that AV conduction is present at such lengthened interval. If AV conduction is present, then the AV interval is lengthened in an appropriate manner, which lengthening may occur abruptly, e.g., in one pacing cycle, or gradually (smoothly), e.g., over several cardiac cycles. Usually, a smooth transitition is preferred as this avoids a sudden jump back to the hysteresis rate. Such smooth transition, when employed, thus progressively slows the basic pacing rate while maintaining the longer or extended AVI, thereby allowing AR pacing to occur at progressively slower rates until either the hysteresis escpae rate is reached, or a native P-wave is sensed that restores control of the patient's rhythm to the patient.

The abruptness or smoothness of the AVI lengthening is preferrably a programmable option. If AV conduction is not present during the test cycle(s), then the shortened value of the AV interval, $AVI_2$, is used for another m cardiac cycles, where m is an integer ranging from 2 to 30. The number m may be the same as the number n (and frequently will be in order to simplify programming of such value), or it may be different. Typically, the number m will be set by the manufacturer of the pacemaker, or it may be programmably selected by the physician during implant, or thereafter. At the conclusion of the m cardiac cycles, the AV interval is again temporarily lengthened to test for AV conduction, and the process repeats.

Figure 9:
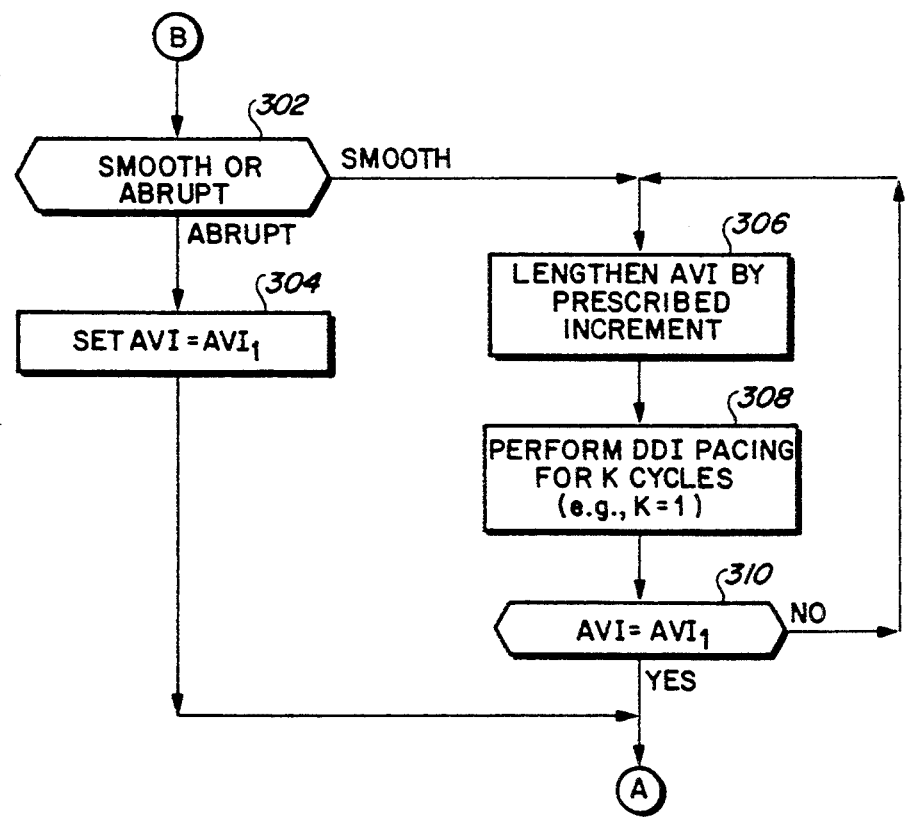
FIGS. 8 and 9 show an expanded portion of the flowchart of FIG. 7 that illustrate the automatic AV interval adjustment feature of the invention.
Figure 8:
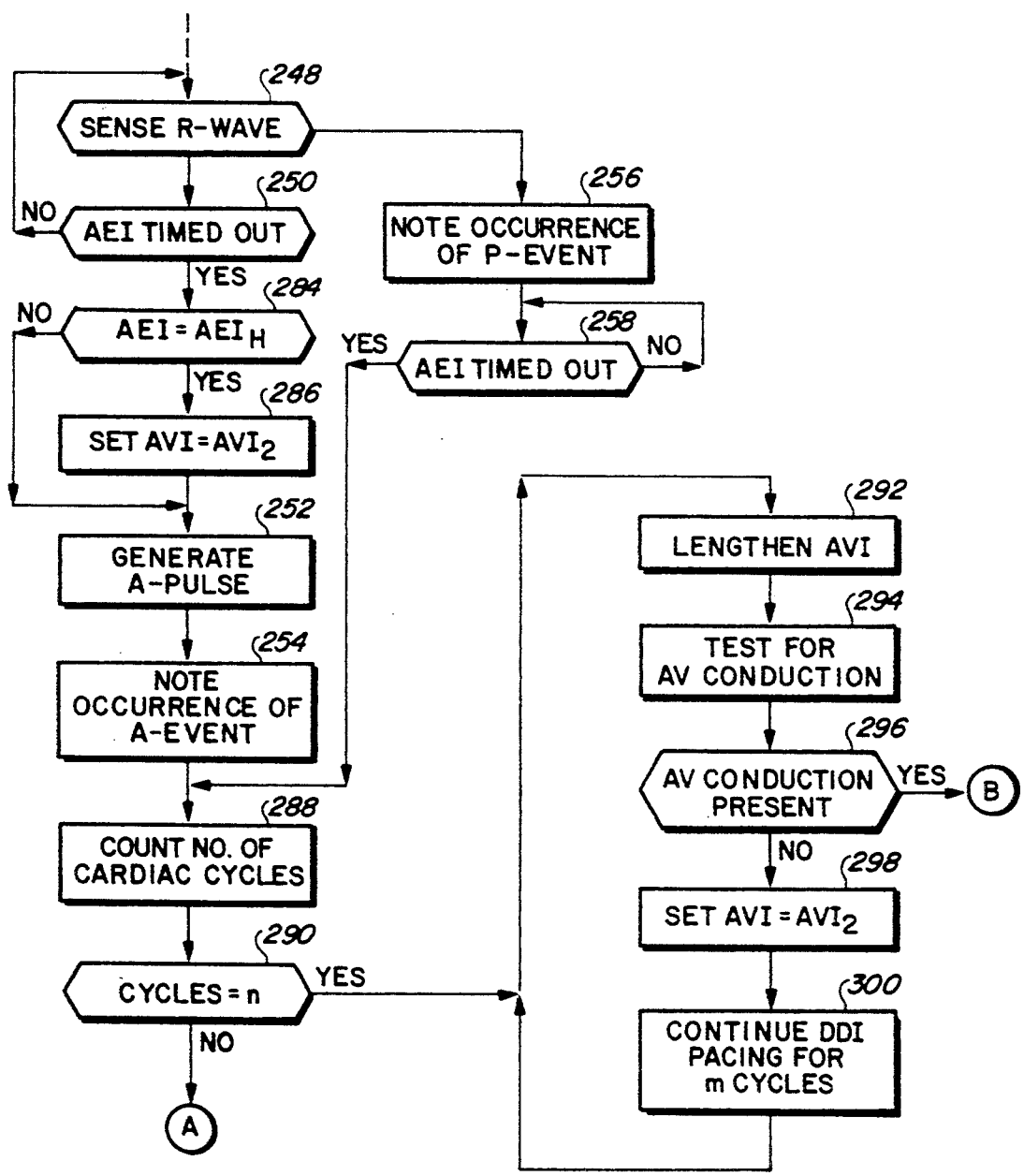

The above-described process of providing PVC-protected DDI hysteresis with automatic AV interval adjustment is further illustrated in the flowcharts of FIGS. 7–9. FIG. 7 is a simplified flowchart that functionally illustrates DDI pacing with PVC-protected hysteresis. FIGS. 8 and 9 are flowcharts that illustrate the automatic adjustment of the AV interval added to the PVC-protected DDI hysteresis method shown in FIG. 7. In each of these flowcharts, each main step or procedure of the method is shown in a "box" or "block," where each box or block has a reference numeral assigned thereto. Such flowcharts provide added insight into the design and operation of the control system 26 (FIG. 1), which control system may be based on specially designed state logic 62 (as shown in FIG. 2), or on a microprocessor-controlled pacemaker (as described, e.g., in the '052 patent, previously referenced). It is submitted that those of skill in the art, given the descriptions of the invention presented herein, including the processes shown in FIGS. 7–9, can readily fashion a pacemaker, and/or operate a pacemaker, that carries out PVC-protected hysteresis with automatic AV interval adjustment in accordance with the present invention.

Referring first to FIG. 7, it is seen that a first step of the method of operating a pacemaker to provide PVC-protected hysteresis in a DDI mode is to begin DDI pacing (block 240). This may seem like a trivial step, but it is included simply to emphasize that most modern implantable pacemakers can be programmed to operate in many different modes. Once the DDI mode has been selected as the operating mode of the pacemaker, the applicable operating parameters are set or otherwise programmed into the pacemaker (block 242). For purposes of the present invention, such operating parameters include, e.g., the programmed (or baseline) atrial escape interval $AEI_1$, the hysteresis atrial escape interval $AEI_H$, the programmed AV interval, $AVI_1$; the shortened AV interval, $AVI_2$; the number of cardiac cycles n during which the shortened AV interval $AVI_2$ is to be used for the first time; the number of cardiac cycles m during which the shortened AV interval $AVI_2$ is to be used after testing for AV conduction and failing; and the like. Note, rather than setting a value of $AEI_H$, or a value of $AVI_2$, a parameter may be defined that indicates how much $AEI_1$ must increase to arrive at $AEI_H$, or how much $AVI_1$ must decrease to arrive at $AVI_2$. Other operating parameters common to all pacing modes, such as the amplitude of the stimulation pulses for the atrial and ventricular channels, the time periods for the BLANK and REFRACTORY time intervals, and the like, are also set or otherwise made available.

Once all the operating parameters have been set or otherwise defined, the operating value of the atrial escape interval AEI is set to $AEI_1$ and the operating value of the VA interval VAI is set to $AVI_1$ (block 244). Next, the timeout of the AEI begins (block 246). If a P-wave is sensed during such timeout (block 248), then a flag (or other logic signal) is set that notes the occurrence of such sensed P-wave (block 256), and the AEI is allowed to finish timing-out (block 258). If no P-wave is sensed during the AEI timeout (blocks 248, 250), then an A-pulse is generated (block 252) as soon as the AEI times-out. Another flag, or equivalent logic signal, is set to note the occurrence of the A-event (block 254), i.e., the generation of the A-pulse.

After the timeout of the AEI, regardless of whether a P-wave was sensed or not, the timeout of the AVI begins (block 260). During the timeout of the AVI, a determination is made as to whether an R-wave occurs (block 262). If not, then upon the timing-out of the AVI (block 264), a V-pulse is generated (block 266), and the occurrence of a "V-event," i.e., the generation of the V-pulse, is noted by setting an appropriate flag or other logic signal (block 268). If an R-wave occurs prior to the timing-out of the AVI (block 262), then the AVI is immediately terminated and a flag (or equivalent logic signal) is set (block 270) indicating such event.

Next, a determination is made as to whether a PR or an AR event has occurred (block 272). Such determination is made by examining the sequence in which the flags (or other logic signals) were set as the various atrial or ventricular events occurred. That is, if a P-flag is set when noting the occurrence of a P-wave (block 256), and an R-flag is set when noting the occurrence of an R-wave (block 270), then the consecutive occurrence of the P-flag and the R-flag signal that a PR event has occurred. It should also be noted that when the control system uses a state machine, as shown in FIG. 2, then the transition of one state to another can also be used to signal specific events that have occurred, and appropriate logic circuitry can then be used to determine that a particular sequence of events, e.g., a PR event, or an AR event, has occurred.

In accordance with an additional feature of the invention, the PR or AR event test that is made at block 272 may further include the requirement that the PR or AR interval associated with such event be greater than a prescribed reference value. Such additional test is suggested in block 272 as the parenthetical statement "(>Ref)."

If a PR or an AR event occurred during the cardiac cycle (as determined at block 272), then the AEI is extended to its hysteresis value, $AEI_H$. If a PR or an AR event did not occur, then the AEI remains at its programmed value, $AEI_1$. If DDI pacing is to continue (block 278), which it typically will unless some sort of interrupt signal, or other command signal is received, then the next cycle begins using whatever value of AEI was set at blocks 274, 276. The next cardiac cycle then begins by starting the AEI (block 246), and the process repeats itself as described above.

Referring next to FIGS. 8 and 9, an expanded flowchart is presented for the steps carried out by the blocks enclosed in the dotted line 282 of FIG. 7. Such expanded flowchart of FIGS. 8 and 9 adds an automatic AV interval adjustment feature to the invention. As seen in FIG. 8, the same steps of determining whether a P-wave is sensed during the timing-out of the AEI (blocks 248, 250), and noting the occurrence of a P-wave if one occurs (block 256), and allowing the AEI to time-out (block 258), as shown in FIG. 7 are included in FIG. 8. Newly added to FIG. 8, after the AEI times-out without having sensed a P-wave (blocks 248, 250), is a step that tests whether the AEI that just timed-out was the extended hysteresis $AEI_H$ or the programmed $AEI_1$ (block 284). If it was the extended $AEI_H$, then the AV interval is set to its shortened value $AVI_2$ (block 286). If not, then there is no change in the AV interval, i.e., it remains at its programmed value, $AV_1$. In either event, an A-pulse is next generated (block 252), and the occurrence of the A-event is noted (block 254).

Still referring to FIG. 8, before the AVI begins, a count is started of the cardiac cycle (block 288). That is, typically a counter (or equivalent) is initially set to zero. Upon the first occurrence of generating an A-pulse after shortening the AVI to $AVI_2$, the counter is incremented. The counter is then incremented for each pacing cycle thereafter. At any given time, the counter thus contains a count of the pacing cycle that is in progress. If the number of pacing cycles that have occurred is less than n, where n is typically a programmed number, e.g., 2–20, then the AVI interval is started and DDI pacing continues to the next pacing cycle as shown in FIG. 7 (blocks 260–278), and the counter is incremented again during the next pass through the loop (blocks 248, 250, 284, 286, 252, 254, 288). If the number of pacing cycles is equal to n (block 290), then the AV interval is temporarily lengthened (block 292). Typically, such lengthening is achieved by simply returning the AV interval back to its programmed value, $AVI_1$. However, it is to be understood that the invention contemplates any lengthening of the AVI in order to test whether AV conduction occurs at the lengthened value.

Once the AV interval has been temporarily lengthened, a test is made for AV conduction (block 294). AV conduction is present if an R-wave occurs as result of conduction through the AV node of the patient's heart. If AV conduction is not present, then the AV interval is returned to its shortened value $AVI_2$ (block 298), and DDI pacing continues for an additional m cardiac cycles (block 300). The value of m is preferably a programmed value. After m cardiac cycles of using the $AVI_2$ shortened value, the AVI is again temporarily lengthened (block 292), and the test for AV conduction (block 294) is again performed (blocks 294, 296).

Should AV conduction be present using the temporarily lengthened AVI (block 296), then the AVI is returned back to its programmed value, $AVI_1$. In returning AVI to its programmed value $AVI_1$, a determination is made, as shown in FIG. 9 (note that FIG. 9 is just a continuation of FIG. 8, joined by the connector block "B"), as to whether an abrupt change or a smooth change should be made (block 302). If an abrupt change is selected, then the AVI is immediately set to $AVI_1$ (block 304), e.g., in one or two cycles. As a practical matter, if the lengthened AVI set at block 292 for the AV conduction test is $AVI_1$, then AVI has already been at the programmed value $AVI_1$ during the AV conduction test for at least one test cycle (where one test cycle is usually all that is required to test for AV conduction). Thus, an abrupt change may simply involve just leaving the AVI at the $AVI_1$ value that was used temporarily during the AV conduction test. If a smooth change is selected (block 302), then the AVI is lengthened by a prescribed increment (block 306), e.g., 5–10 msec., and DDI pacing is performed using the slightly lengthened AVI for a prescribed number k of cardiac cycles, e.g., one or two cardiac cycles (block 308). Then, if the AVI is not yet at the programmed $AVI_1$ (determined at block 310), then the AVI is again lengthened by the prescribed increment (block 306). This process (blocks 306, 308, 310) continues until the AVI has been gradually increased to its programmed value, $AVI_1$, thereby providing for a smooth transition from the shortened $AVI_2$ to the programmed $AVI_1$.

Normally, $AVI_2$ will be about 50 or 75 msec shorter than $AVI_1$. The value of $AVI_2$ may be a fixed amount less than the programmed $AVI_1$, e.g., $AVI_2$ will always be a fixed amount (50 or 75 msec) less than whatever the value of $AVI_1$ is programmed to be. Alternatively, the value of $AVI_2$ may be selected to be one of a plurality of programmed intervals. If the value of $AVI_2$ is a programmable option, then the first option should start at about 25 msec shorter than the programmable $AVI_1$ value, with the possibility of programming $AVI_2$ as low as the shortest programmable $AVI_1$.

As described above, it is thus seen that the present invention provides a PVC-protected hysteresis function in a dual-chamber pacemaker operating in the DDI mode. It is also seen that the invention minimizes the chance that such DDI operation might result in sustained functional atrial pacing at the slower hysteresis rate by automatically shortening the AV interval upon the occurrence of an A-pulse following the extended (hysteresis) atrial escape interval. It is further seen that, subsequent to shortening the AV interval, the invention subsequently tests for AV conduction at a longer AV interval, and if such test is successful, reinstates (either abruptly or gradually) the original programmed value of the AV interval.

While the invention herein disclosed has been described by means of specific embodiments and applications thereof, numerous modifications and variations could be made thereto by those skilled in the art without departing from the scope of the invention set forth in the claims. For example, while the invention has been described in terms of a PVC-protected DDI mode of operation, the principle of providing PVC-protected hysteresis (of invoking the extended hysteresis atrial escape interval only upon the occurrence of a PR event or an .AR event) may also find applicability with other pacemaker operating modes. Further, the principle of automatically shortening the AV interval after using an extended hysteresis atrial escape interval in order to reduce the likelihood of sustained functional atrial pacing at the hysteresis rate (which may be too slow), and then subsequently lengthening the AV interval back to its original programmed value after the risk of such sustained functional atrial pacing has been minimized, may also find applicability to other pacing modes.

What is claimed is:

1. A dual-chamber implantable pacemaker having a hysteresis DDI mode of operation comprising:
   an atrial channel comprising an atrial pulse generator and an atrial sense amplifier;
   a ventricular channel comprising a ventricular pulse generator and a ventricular sense amplifier;
   timing means for defining an atrial escape interval (AEI) and an AV interval, said AEI assuming one of at least two programmable values, a first value $AEI_1$ comprising a normal atrial escape interval, and a second value $AEI_H$ comprising a hysteresis atrial escape interval;
   a control circuit for controlling the atrial channel and the ventricular channel, said control circuit comprising:
   (1) means for initiating an atrial pulse (A-pulse) to be generated by said atrial pulse generator when the AEI terminates, unless an atrial event (P-wave) is sensed by the atrial sense amplifier during the AEI, in which case the A-pulse is inhibited from being generated;
   (2) means for initiating a ventricular pulse (V-pulse) to be generated by said ventricular pulse generator when the AV interval terminates, unless a ventricular event (R-wave) is sensed by the ventricular sense amplifier during the AV interval, in which case the V-pulse is inhibited from being generated;
   (3) means for initiating the AEI to begin upon the occurrence of an R-wave or a V-pulse, said AEI assuming said hysteresis $AEI_H$ value only upon the occurrence of: (a) an R-wave following a P-wave (a PR event), or (b) an R-wave following an A-pulse (an AR event), and assuming said normal $AEI_1$ value at all other times; and
   (4) means for initiating the AV interval to begin following the AEI;
   wherein the consecutive occurrence of said AEI and said AV interval comprises a cardiac cycle.

2. The pacemaker, as set forth in claim 1, wherein the control circuit further includes means for measuring a time interval between a P-wave and a succeeding R-wave of a PR event (a PR event interval), and between an A-pulse and a succeeding R-wave of an AR event (an AR event interval), and wherein the control circuit causes the AEI to assume said second value $AEI_H$ only when the determined PR or AR event interval exceeds a prescribed reference interval.

3. The pacemaker, as set forth in claim 1, wherein said AV interval is a first value, $AVI_1$, and further wherein said control circuit causes said AV interval to assume a second value, $AVI_2$, shorter than said first value $AVI_1$, for a prescribed number n of cardiac cycles, whenever an A-pulse is generated by said atrial pulse generator following an AEI of said second value, $AEI_H$.

4. The pacemaker, as set forth in claim 3, wherein said control circuit, after said prescribed number n of cardiac cycles using said AV interval of said second value, $AVI_2$, causes said AV interval to temporarily assume said first value, $AVI_1$, for at least one test cardiac cycle, and wherein after said at least one test cardiac cycle said control circuit further causes:
   said AV interval to assume said second value, $AVI_2$, for a prescribed number m of cardiac cycles provided a V-pulse is generated by said ventricular pulse generator when the AV interval of said at least one test cardiac cycle terminates, and
   said AV interval to permanently return to said first value, $AVI_1$, provided an R-wave is sensed by said ventricular sensing means prior to the AV interval of said at least one test cardiac cycle terminating.

5. The pacemaker, as set forth in claim 4, wherein said control circuit causes said AV interval to return to said first value $AVI_1$ in a single cardiac cycle, whereby an abrupt transition from said second value $AVI_2$ to said first value $AVI_1$ is provided for said AV interval.

6. The pacemaker, as set forth in claim 4, wherein said control circuit causes said AV interval to return to said first value $AVI_1$ in incremental steps over a plurality of cardiac cycles, whereby a smooth transition from said second value $AVI_2$ to said first value $AVI_1$ is provided for said escape interval.

7. A dual-chamber implantable pacemaker comprising:
   an atrial channel that includes means for sensing P-waves and means for generating A-pulses;
   a ventricular channel that includes means for sensing R-waves and means for generating V-pulses;
   a control system that controls the operation of said atrial channel and ventricular channel so as to operate said implantable pacemaker in a DDI hysteresis mode, said control system including:
   timing means for defining an atrial escape interval (AEI) and an AV interval, the sequential occurrence of said AEI and said AV interval comprising a cardiac cycle, with the AV interval beginning at the conclusion of the AEI, and with the AEI beginning at the conclusion of the AV interval or upon the occurrence of an R-wave, whichever event occurs first in a given cardiac cycle;
   control means for: (1) causing an A-pulse to be generated in said atrial channel only upon the timing-out of said AEI without having sensed a P-wave during said AEI; (2) inhibiting the generation of an A-pulse in said atrial channel only upon sensing a P-wave in said atrial channel prior to the timing-out of said AEI; (3) causing a V-pulse to be generated in said ventricular channel only upon the timing-out of said AV interval without having sensed an R-wave during said AV interval; (4) inhibiting the generation of a V-pulse in said ventricular channel only upon sensing an R-wave in said ventricular channel prior to the timing-out of said AV interval; and (5) immediately terminating said AV interval upon the sensing of an R-wave in said ventricular channel prior to the timing-out of said AV interval;
   said AEI being defined by said timing means to assume a first interval value $AEI_1$ following the generation of a V-pulse in said ventricular channel,, and a second interval value $AEI_H$ comprising a hysteresis AEI value following a PR event or an AR event, a PR event comprising an K-wave following a P-wave, and an AR event comprising an R-wave following an A-pulse, said AV interval value being defined by said timing means to assume a first AV interval value AVI- following the termination of said AEI, regardless of whether said AEI has assumed said first interval value $AEI_1$ or said second interval value $AEI_H$;

a memory circuit coupled to said control system for storing control signals associated with the operation of said control system, said control signals including at least one AEI value signal and at least one AVI value signal, said $AEI_1$, $AEI_H$, and $AVI_1$ values being defined by said timing means as a function of said at least one AEI and AVI value signals; and telemetry means for allowing said control signals to be programmed into said memory circuit from a location external to said implantable pacemaker.

8. The dual-chamber implantable pacemaker, as defined in claim 7, wherein said timing means of said control system is further for determining a time interval between an atrial event and a succeeding R-wave (an atrial/R interval), and wherein the AEI is defined by said timing means to assume said $AEI_H$ value only when the determined atrial/R interval exceeds a prescribed reference interval.

9. The dual-chamber implantable pacemaker, as defined in claim 8, wherein said prescribed reference interval comprises one of said control signals programmed into said memory circuit via said telemetry means.

10. The dual-chamber implantable pacemaker, as defined in claim 8, wherein said prescribed reference interval comprises a time interval commonly within a range of 80 to 130 milliseconds, but programmable by the physician.

11. The dual-chamber implantable pacemaker, as defined in claim 7, wherein $AEI_H$ is longer than $AEI_1$, and wherein the timing means of said control system defines said AV interval to assume a shortened AV interval value, $AVI_2$, where $AVI_2$ is less than $AVI_1$, for a prescribed number n of cardiac cycles, whenever an A-pulse is generated within said atrial channel following an AEI of said second interval value, $AEI_H$.

12. The dual-chamber implantable pacemaker, as defined in claim 11, wherein said control system, after said prescribed number n of cardiac cycles with said AV interval assuming said shortened AV interval value, $AVI_2$, causes said AV interval to temporarily assume a lengthened AV interval value for at least one test cardiac cycle, and wherein after said at least one test cardiac cycle the timing means of said control system further defines:

said AV interval to assume said shortened AV interval value $AVI_2$ for a prescribed number m of cardiac cycles provided a V-pulse is generated in said ventricular channel when the temporarily lengthened AV interval of said at least one test cardiac cycle terminates, and said AV interval to assume said first AV interval value $AVI_1$ that provided an AR event or a PR event concludes during said temporarily lengthened escape interval of said at least one test cardiac cycle.

13. The dual-chamber implantable pacemaker, as defined in claim 12, wherein the prescribed number n of cardiac cycles is equal to the prescribed number m of cardiac cycles.

14. The dual-chamber implantable pacemaker, as defined in claim 12, wherein the timing means of said control system causes said AV interval to return to said first AV interval value $AVI_1$ in a single cardiac cycle, whereby said AV interval abruptly changes from said $AVI_2$ interval value to said $AVI_1$ interval value.

15. The dual-chamber implantable pacemaker, as defined in claim 12, wherein the timing means of said control system causes said AV interval to return to said first AV interval value $AVI_1$ in incremental steps over a plurality of cardiac cycles, whereby said AV interval smoothly changes from said $AVI_2$ interval value to said $AVI_1$ interval value.

16. A method of operating a dual-chamber implantable pacemaker so that it operates in a DDI hysteresis mode, said dual-chamber implantable pacemaker including: (1) an atrial channel that includes atrial sensing means for sensing a P-wave and atrial pacing means for generating an A-pulse, (2) a ventricular channel that includes ventricular sensing means for sensing an R-wave and ventricular pacing means for generating a V-pulse, and (3) a control system that monitors the atrial and ventricular sensing means and controls the atrial and ventricular pacing means in accordance with the DDI hysteresis mode of operation, said method comprising the steps of:

(a) defining two possible values for an atrial escape interval, AEI, to used by said control system, a first value $AEI_1$ comprising a normal AEI, and a second value $AEI_H$ comprising a hysteresis AEI, with $AEI_H$ being longer than $AEI_1$;

(b) defining an AV interval, AVI, to be used by said control system;

(c) initially setting AEI to one of said $AEI_1$ or $AEI_H$;

(d) starting the AEI;

(e) sensing whether a P-wave occurs before the AEI times out; and, if so, inhibiting the generation of an A-pulse upon the timing-out of the AEI; and, if not so, generating an A-pulse upon the timing-out of the AEI;

(f) starting the AVI upon the AEI timing-out;

(g) sensing whether an R-wave occurs in the ventricular channel prior to the AVI timing out, and (1) if so, terminating the AVI immediately upon the sensing of the R-wave, inhibiting the generation of a V-pulse, and determining whether the sensed R-wave represents the culmination of a PR event or an AR event, a PR event comprising a P-wave sensed in the atrial channel followed by an R-wave sensed in the ventricular channel, and an AR event comprising an A-pulse generated in the atrial channel followed by an R-wave sensed in the ventricular channel, and (2) if not so, generating a V-pulse immediately upon the AVI timing out;

(h) setting the AEI to $AEI_H$ only if an R-wave is sensed in step (g) and if said sensed R-wave represents the culmination of a PR event or an AR event;

(i) setting the AEI to $AEI_1$ if a V-pulse is generated in step (g);

(j) starting the AEI immediately upon the termination of the AVI, if an R-wave is sensed in step (g), or immediately upon the AVI timing-out if an R-wave is not sensed in step (g); and (h) repeating steps (e)–(j) for so long as the DDI hysteresis mode of operation is to continue.

17. The method, as set forth in claim 16, further including as part of step (g) determining a time interval between the A-pulse and the R-wave of an AR event, or a time interval between the P-wave and the R-wave of a PR event, whichever AR or PR event occurs, and wherein step (h) comprises setting the AEI to $AEI_H$ only if an R-wave is sensed in step (g) and if the determined time interval between the A-pulse and the R-wave of the AR event, or between the P-wave and the R-wave of the PR event, is greater than a prescribed reference time interval.

18. The method, as set forth in claim 16, wherein step (b) comprises defining two possible values for said AV interval, $AVI_1$ and $AVI_2$, with $AVI_1$ being greater than $AVI_2$, and initially using $AVI_1$ as the value of the AVI, but switching to using $AVI_2$ as the value of the AVI upon the generating of an A-pulse when the AEI concludes provided the AEI has assumed said $AEI_H$ value, and continuing to use $AVI_2$ as the value of the AVI during the DDI hysteresis mode of operation for at least a prescribed number n of cardiac cycles, a cardiac cycle comprising a consecutive occurrence of the AEI and the AVI.

19. The method, as set forth in claim 18, wherein, after said prescribed number n of cardiac cycles, said method further includes:
momentarily lengthening the AVI;
returning the value of the AVI back to $AVI_2$ provided the momentarily lengthened AVI times-out without an R-wave having been sensed, and reinstating the value of the AVI to $AVI_1$ in the event that an R-wave is sensed prior to the timing-out of the momentarily lengthened AVI.

20. The method, as set forth in claim 19, wherein the step of momentarily lengthening of the AVI comprises setting AVI to $AVI_1$ for one cardiac cycle.

21. The method, as set forth in claim 19, wherein the step of reinstating the value of the AVI to $AVI_1$ comprises abruptly setting AVI to $AVI_1$.

22. The method, as set forth in claim 19, wherein the step of reinstating the value of the AVI to $AVI_1$ comprises gradually returning the value of AVI to $AVI_1$ from $AVI_2$.

23. The method, as set forth in claim 19, wherein the step of returning the value of the AVI back to $AVI_2$ in the event that the momentarily lengthened AVI times-out without an R-wave having been sensed comprises returning the value of the AVI back to $AVI_2$ over a prescribed number m of cardiac cycles.

24. The method, as set forth in claim 23, wherein the prescribed number n of cardiac cycles equals the prescribed number m of cardiac cycles.

* * * * *